(12) United States Patent
Chen et al.

(10) Patent No.: US 9,457,007 B2
(45) Date of Patent: Oct. 4, 2016

(54) PRENYLFLAVANONE COMPOUNDS FOR MODULATING DIABETES

(71) Applicant: NATUREWISE BIOTECH & MEDICALS CORPORATION, Taipei (TW)

(72) Inventors: Chia-Nan Chen, Taipei (TW); Li-Ling Chi, Taipei (TW)

(73) Assignee: NATUREWISE BIOTECH & MEDICALS CORPORATION, Taipei (TW)

( * ) Notice: Subject to any disclaimer, the term of this patent is extended or adjusted under 35 U.S.C. 154(b) by 0 days.

(21) Appl. No.: 14/226,080

(22) Filed: Mar. 26, 2014

(65) Prior Publication Data

US 2014/0296543 A1    Oct. 2, 2014

Related U.S. Application Data

(60) Provisional application No. 61/806,553, filed on Mar. 29, 2013.

(51) Int. Cl.
*A61K 31/353* (2006.01)
*C07D 311/32* (2006.01)
*A61K 35/644* (2015.01)

(52) U.S. Cl.
CPC .......... *A61K 31/353* (2013.01); *A61K 35/644* (2013.01); *C07D 311/32* (2013.01)

(58) Field of Classification Search
USPC ....................................................... 549/403
See application file for complete search history.

(56) References Cited

U.S. PATENT DOCUMENTS

| | | |
|---|---|---|
| 2006/0292204 A1 | 12/2006 | Kumazawa et al. |
| 2007/0092551 A1 | 4/2007 | Enoki et al. |
| 2007/0161579 A1 | 7/2007 | Kumazawa et al. |
| 2009/0076130 A1 | 3/2009 | Huang et al. |
| 2010/0144857 A1 | 6/2010 | Huang et al. |
| 2011/0020462 A1 | 1/2011 | Huang et al. |
| 2012/0059052 A1 | 3/2012 | Kuhrts |

FOREIGN PATENT DOCUMENTS

| | | |
|---|---|---|
| CN | 102885854 A | 1/2013 |
| EP | 2 277 387 A1 | 1/2011 |
| JP | 2005-029560 A | 2/2005 |
| JP | 2005-029778 A | 2/2005 |
| JP | 2005-272374 A | 10/2005 |
| JP | 2010-195762 A | 9/2010 |
| JP | 2011-024559 A | 2/2011 |
| WO | WO 2009/014315 | 1/2009 |

OTHER PUBLICATIONS

Narvaez-Mastache et al., Antihyperglycemic Activity and Chemical Constituents of Eysenhardtia platycarpa, 2006, J. Nat. Prod., 69, 1687-1691.*
Office action and Search Report issued on Jun. 24, 2014 by the European Patent Office (EPO) for counterpart European application 14162211.8.
T. Annadurai et al: "Antihyperglycemic and antioxidant effects of a flavanone, naringenln, in streptozotocni—coti nicotinamide-induced experimental diabetic rats", Journal of Physiology and Biochemistry,vol. 68, No. 3, Jan. 11, 2012, pp. 307-318.
Long Cui et al: "New Prenylated Flavanones from Erythrina abyssinica with Protein Tyrosine Phosphatas 1B (PTPIB) Inhibitory Activity", Planta Medica, vol. 76, No. 07, Dec. 3, 2009 , pp. 713-718.
Dan Christensen et al: "Histone Deacetylase (HDAC) Inhibition as a Novel Treatment for Diabetes Mellitus", Molecular Medicine, vol. 17, No. 5-6, Jan. 1, 2011.
Ales Zima et al: "Anti radical and Cytoprotective Activities of Several C-Geranyl-substituted Flavanones from Paulowina tomentosa Fruit", Molecules, vol. 15, No. 9, Aug. 31, 2010, pp. 6035-6049.
Office action dated Jun. 19, 2015 for counterpart Japanese Application No. 2014-066426.
English translation of the Office action dated Jun. 19, 2015 for counterpart Japanese Application No. 2014-066426.
Christensen, Dan P. et al., Histone Deacetylase (HDAC) Inhibition as a Novel Treatment for Diabetes Mellitus, Molecular Medicine, 2011, vol. 17, No. 5-6, pp. 378-390.
US2006/0292204 is the counterpart for JP 2005-029778 A.
US20070161579 is the counterpart for JP 2005-029560 A.
English translation of JP 2005-272374 A.
US20110020462 is the counterpart to JP 2011-024559 A.
English translation of JP 2010-195762 A.
Office Action dated Mar. 31, 2016 issued by KIPO for corresponding Korean patent application 10-2014-0037736.
English translation of the Office Action dated Mar. 31, 2016 issued by KIPO for corresponding Korean patent application 10-2014-0037736.
Office Action dated Apr. 15, 2015 issued by Australian IP Office for corresponding Australian patent application 2014201835.
Huang, W-J., et al, "NBM-HD-3, a novel histone deacetylase inhibitor with anticancer activity through modulation of PTEN and AKT in brain cancer cells". Journal of Ethnopharmacology, 2011, vol. 136, pp. 156-167.
Miguel, M.G. and Antunes, M.D. "Is propolis safe as an alternative medicine?". Journal of Pharmacy And Bioallied Sciences, 2011, vol. 3, No. 4, pp. 479-495.
Office Action and search report dated May 9, 2016 issued by China State Intellectual Property Office for corresponding China patent application 201410123171.3.
English translation of the search report dated May 9, 2016 issued by China State Intellectual Property Office for corresponding China patent application 201410123171.3.
Chen, C-N., "Most Recent Research on Taiwanese Green Propolis and Mainland China Propolis". Taiwan Bee and Bee Product Association Special Edition, 2012, pp. 89-103.

(Continued)

*Primary Examiner* — Kristin Vajda
*Assistant Examiner* — Andrew D Kosar
(74) *Attorney, Agent, or Firm* — WPAT, P.C., Intellectual Property Attorneys; Anthony King

(57) ABSTRACT

The present invention is directed to a novel use of prenylflavanone compounds for control of blood glucose and treatment or prevention of diabetes.

4 Claims, 16 Drawing Sheets

(56) References Cited

OTHER PUBLICATIONS

Guo Fangbin, "Analysis on the Effect and Mechanism of Propolis on Diabetes," Apicultural Science and Technology, No. 5, pp. 32-34 and 48, 2004.
English abstract translation of CN102885854A, 2013.
English abstract translation of Chen, C-N., "Most Recent Research on Taiwanese Green Propolis and Mainland China Propolis". Taiwan Bee and Bee Product Association Special Edition, 2012, pp. 89-103.
English abstract translation of Guo Fangbin, "Analysis on the Effect and Mechanism of Propolis on Diabetes," Apicultural Science and Technology, No. 5, pp. 32-34 and 48, 2004.

* cited by examiner

PRENYLFLAVANONE COMPOUNDS FOR MODULATING DIABETES

FIELD OF THE INVENTION

The present invention relates to a novel use of prenylflavanone compounds in the preparation of a composition for modulation of blood glucose, preferably for treatment or prevention of diabetes.

DESCRIPTION OF THE RELATED ART

Diabetes has been known in Egypt from about 1500 years B.C.[1-2]; however, its pathogenic mechanism was gradually understood after 1900 years A.D. From World Health Organization (WHO) statistics, there were about 3.46 hundred million people suffering from diabetes all over the world, in which the patients suffering from type II diabetes (i.e., non-insulin-dependent diabetes) prevailed.

Diabetes is a disease with metabolic abnormalities of saccharide. Occurrence of such disease is relevant to hypoinsulinism in the body and frequently results in excesses in dieting, drinking and urine, weight loss and conditions such as hyperglycemia and high glucose in urine. Insulin is a hormone primarily for controlling absorption and utilization of glucose in the muscular and fat tissue cells in the body. In case of insulin deficiency, glucose in the blood fails to enter into these tissue cells for utilization, causing hyperglycemia and serious effects.

Diabetes is classified by the WHO into four groups[3]: (1) type I diabetes (insulin-dependent); (2) type II diabetes (non-insulin-dependent); (3) secondary diabetes; and (4) gestational diabetes. Such four types of diabetes differ in mechanism and cause; however, they are comparatively similar in pathological features as a result of insufficient insulin secretion from Langerhans islet beta cells in the pancreas, which fails to reduce blood glucose concentration and causes hyperglycemia.

Type I Diabetes frequently occurs in children, mostly as a result of suffering from the autoimmune diseases which cause beta cells to be damaged and fail to secret insulin. Type II diabetes frequently occurs in middle-aged adults and is possibly caused by lifestyle and obesity. For molecular mechanism, it is likely that the beta cells are damaged in part, causing insufficient insulin secretion; or, although sufficient in secretion, insulin fails to normally bind to the insulin receptor on the surface of the tissue cells and thus fails to induce glucose into the cells for further utilization; or, it results from other unknown causes. Similar to type II diabetes, the gestational diabetes might be caused by interference effects from hormones; however, after giving birth to a child, the interference effects from hormones return back to normal levels.

As drugs for control and treatment of diabetes, insulin and a number of oral drugs for modulation of blood glucose have been on the market for the past few decades but are still less effective for controlling blood glucose and do not cure type I or II diabetes. It is not fearful for diabetes itself, but the complications resulting from it are the most leading causes killing patients. Such complications from diabetes include hypoglycemia, ketoacidosis, cardiovascular diseases, chronic renal failure, retinopathy, neuropathy and microangiopathy.

According to studies and statistics, those suffering from type II diabetes comprise about 90% of all of the diabetes patients[4]. The oral antihyperglycemics are the leading therapeutic drugs for type II diabetes, which are classified as follows[5]: biguanides, sulfaureas, thiazolidiones, meglitinides, α-glycosidase inhibitors, and dipeptidyl peptidase-4 (DPP-4) inhibitors.

Biguanide drugs can reduce blood glucose through reducing glucose output from the liver and improving insulin resistance as the primary mechanism of action. Biguanide drugs include metformin, phenformin and buformin. Sulfaurea drugs can reduce blood glucose through stimulating the islet beta cells to secret insulin as the primary mechanism of action to increase the level of insulin in body. Sulfaurea drugs include tobutamide, acetohexamide, tolazamide and chlorpropamide. Thiazolidione drugs can reduce blood glucose through enhancing the sensitivity of the target cells to insulin effects as the primary mechanism of action. Thiazolidione drugs include rosiglitazone, pioglitazone, and troglitazone. Meglitinide drugs can reduce postprandial blood glucose through stimulating early secretion of insulin as the primary mechanism of action. Meglitinide drugs include repaglinide and nateglinide. α-Glycosidase inhibitors can reduce postprandial blood glucose through inhibition of absorption of carbohydrates in the upper part of the small intestine as the primary mechanism of action. α-Glycosidase inhibitors include miglitol, acarbose and voglibose. Dipeptidyl peptidase-4 (DPP-4) inhibitors can enhance activity of GLP-1 in the body and prolong time of action of GLP-1 in the body by inhibition of DPP-4. Dipeptidyl peptidase-4 (DPP-4) inhibitors include vildagliptin, sitagliptin, saxagliptin and linagliptin. The above-mentioned drugs can achieve modulations of blood glucose and prevention of the development of diseases only, but diabetes cannot be cured thereby. Therefore, it remains an important challenge for the development of more reliable and more effective therapeutic drugs for diabetes at present.

Propolis is a colorized gummy substance formed by mixing the juice from plant burgeons picked by bees, or by mixing secreta from a pericarp outer layer, with beeswax. Propolis is an important substance for bees for restoration of honeycomb and resistance to invasion of the pathogenic bacteria, so it plays an important role in breeding and survival of bee colonies[6]. It has been a history of hundreds of years for humans to use propolis as a conventional medicine[7]. At present, propolis has been widely used as the raw material for natural health foods.

It was found in a study that propolis had a wide range of biological activities, including such activities as antibiosis[8], antivirus[9], anticancer[10], immune regulation[11], protection of liver[12], and modulation of blood glucose[13] and antioxidation[14]. Because plant origins for producing propolis in different areas in different seasons vary, propolis would have different active components. At present, propolis can be classified into six types around the world, and the propolis having propolins as the main component, found only in Taiwan[15-22], Okinawa Japan[23-26] and the Solomon Islands[27], has the international classification of Pacific Propolis.

The propolis produced in Taiwan is called Taiwan Green Propolis, which is produced in summer, has the primary active components isolated and identified as prenylflavanones, and is known to include 10 active components of propolins A to J (PPA-PPJ)[28]. It is known from present studies that Taiwan Green Propolis has the primary biological activities of neuro-nourish, anti-cancer, antibiosis and antioxidation. There are no reports or prior arts indicating or predicting that Taiwan Green Propolis or prenylflavanones is associated with blood glucose.

REFERENCES

1. Ripoll, Brian C. Leutholtz, Ignacio. Exercise and disease management. 2nd ed. Boca Raton: CRC Press: 25. ISBN 978-1-4398-2759-8.

2. editor, Leonid Poretsky, Principles of diabetes mellitus. 2nd ed. New York: Springer. 2009: 3. ISBN 978-0-387-09840-1.
3. Diabetes, World Health Organization. September 2011 (2011 Sep. 15]).
4. Bergenstal R M, Wysham C, Macconell L, Malloy J, Walsh B, Yan P, Wilhelm K, Malone J, Porter L E, DURATION-2 Study Group. Efficacy and safety of exenatide once weekly versus sitagliptin or pioglitazone as an adjunct to metformin for treatment of type 2 diabetes (DURATION-2): a randomised trial. The Lancet, 376 (9739):431-9.
5. The Guidelines on Prevention of Diabetes II in China 2010.
6. Burdock G A. Review of the biological properties and toxicity of bee propolis (propolis). Food Chem. Toxicol. 1998, 36, 347-363.
7. Daugsch A, Moraes C S, Fort P, Park Y K. Brazilian red propolis-chemical composition and botanical origin. Evid Based Complement Alternat Med. 2008, 5, 435-441.
8. Drago L, De Vecchi E, Nicola L, Gismondo M R. In vitro antimicrobial activity of a novel propolis formulation (Actichelated propolis). J Appl Microbiol. 2007, 103, 1914-1921.
9. Shimizu T, Hino A, Tsutsumi A, Park Y K, Watanabe W, Kurokawa M. Anti-influenza virus activity of propolis in vitro and its efficacy against influenza infection in mice. Antivir Chem. Chemother. 2008, 19, 7-13.
10. Watanabe M A, Amarante M K, Conti B J, Sforcin J M. Cytotoxic constituents of propolis inducing anticancer effects: a review. J Pharm Pharmacol. 2011, 63, 1378-1386.
11. Orsatti C L, Missima F, Pagliarone A C, Bachiega T F, Búfalo M C, Arújo J P Jr, Sforcin J M. Propolis immunomodulatory action in vivo on Toll-like receptors 2 and 4 expression and on pro-inflammatory cytokines production in mice. Phytother Res. 2010 August; 24 (8):1141-6.
12. Nakamura T, Ohta Y, Ohashi K, Ikeno K, Watanabe R, Tokunaga K, Harada N. Protective Effect of Brazilian Propolis Against Hepatic Oxidative Damage in Rats with Water-immersion Restraint Stress. Phytother Res. 2012 Feb. 1. doi: 10.1002/ptr.460
13. Zhu W, Chen M, Shou Q, Li Y, Hu F. Biological activities of chinese propolis and brazilian propolis on streptozotocin-induced type 1 diabetes mellitus in rats. Evid Based Complement Alternat Med. 2011; 2011: 468529.
14. Tsai Y C, Wang Y H, Liou C C, Lin Y C, Huang H, Liu Y C. Induction of oxidative DNA damage by flavonoids of propolis: its mechanism and implication about antioxidant capacity. Chem Res Toxicol. 2012 Jan. 13; 25 (1):191-6.
15. Chen C N, Wu C L, Shy H S, Lin J K. Cytotoxic prenylflavanones from Taiwanese propolis. J Nat. Prod. 2003 April; 66 (4):503-6.
16. Chen C N, Wu C L, Lin J K. Propolin C from propolis induces apoptosis through activating caspases, Bid and cytochrome c release in human melanoma cells. Biochem Pharmacol. 2004 Jan. 1; 67 (1):53-66.
17. Chen C N, Weng M S, Wu C L, Lin J K. Comparison of Radical Scavenging Activity, Cytotoxic Effects and Apoptosis Induction in Human Melanoma Cells by Taiwanese Propolis from Different Sources. Evid Based Complement Alternat Med. 2004 Sep. 1; 1 (2):175-185.
18. Chen C N, Wu C L, Lin J K. Apoptosis of human melanoma cells induced by the novel compounds propolin A and propolin B from Taiwanese propolis. Cancer Lett. 2007 Jan. 8; 245 (1-2):218-31.
19. Weng M S, Liao C H, Chen C N, Wu C L, Lin J K. Propolin H from Taiwanese propolis induces G1 arrest in human lung carcinoma cells. J Agric Food Chem. 2007 Jun. 27; 55 (13):5289-98.
20. Huang W J, Huang C H, Wu C L, Lin J K, Chen Y W, Lin C L, Chuang S E, Huang C Y, Chen C N. Propolin G, a prenylflavanone, isolated from Taiwanese propolis, induces caspase-dependent apoptosis in brain cancer cells. J Agric Food Chem. 2007 Sep. 5; 55 (18):7366-76.
21. Chen Y W, Wu S W, Ho K K, Lin S B, Huang C Y, Chen C C. Characterisation of Taiwanese propolis collected from different locations and seasons. Journal of the Science of Food and Agriculture. January/2008; 88:412-419.
22. Popova M, Chen C N, Chen P Y, Huang C Y, Bankova V. A validated spectrophotometric method for quantification of prenylated flavanones in pacific propolis from Taiwan. Phytochem Anal. 2010 March; 21 (2):186-91.
23. Chen C N, Hsiao C J, Lee S S, Guh J H, Chiang P C, Huang C C, Huang W J. Chemical modification and anticancer effect of prenylated flavanones from Taiwanese propolis. Nat Prod Res. 2012; 26 (2):116-24.
24. Kumazawa S, Goto H, Hamasaka T, Fukumoto S, Fujimoto T, Nakayama T. A new prenylated flavonoid from propolis collected in Okinawa, Japan. Biosci Biotechnol Biochem. 2004 January; 68 (1):260-2.
25. Kumazawa S, Ueda R, Hamasaka T, Fukumoto S, Fujimoto T, Nakayama T. Antioxidant prenylated flavonoids from propolis collected in Okinawa, Japan. J Agric Food Chem. 2007 Sep. 19; 55 (19):7722-5.
26. Kumazawa S, Nakamura J, Murase M, Miyagawa M, Ahn M R, Fukumoto S. Plant origin of Okinawan propolis: honeybee behavior observation and phytochemical analysis. Naturwissenschaften. 2008 August; 95 (8):781-6.
27. Raghukumar R, Vali L, Watson D, Fearnley J, Seidel V. Antimethicillin-resistant *Staphylococcus aureus* (MRSA) activity of 'pacific propolis' and isolated prenylflavanones. Phytother Res. 2010 August; 24 (8):1181-7.
28. TW 201304789 A1.

DETAILED DESCRIPTION OF THE INVENTION

Figure 1:
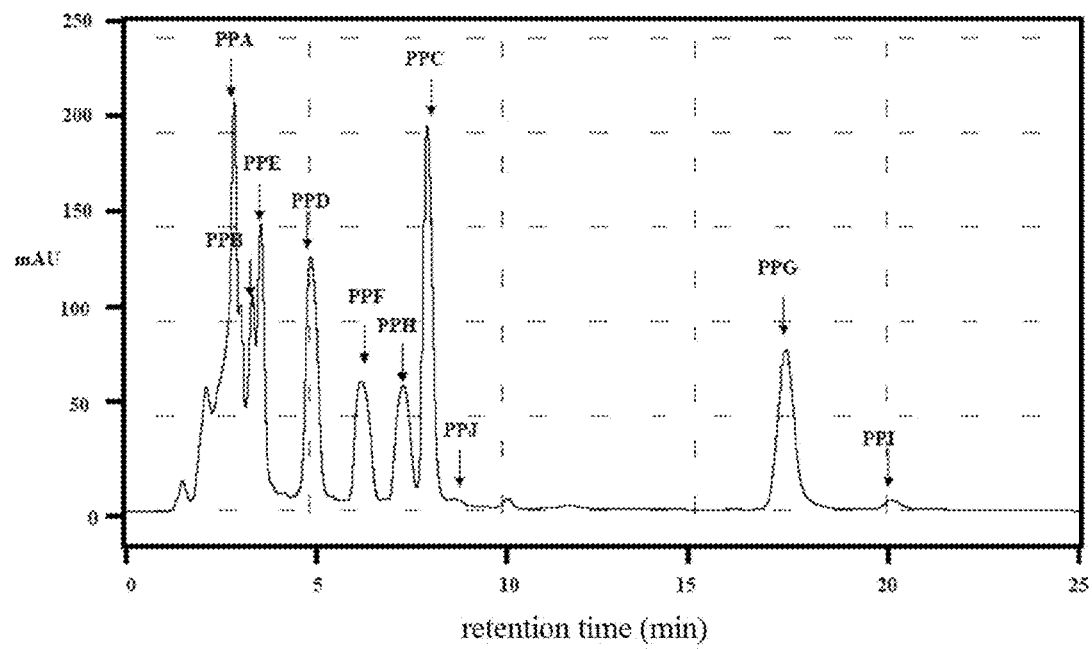
FIG. 1 is a diagram of HPLC analysis of Taiwan Green Propolis alcohol extract (TPE).

The present invention unexpectedly found that prenylflavanone compounds have effects on the modulation of blood glucose, thereby treating diabetes.

The present invention provides a novel use of prenylflavanone compounds in the preparation of a composition for modulating blood glucose, wherein the prenylflavanone compounds have formula (1):

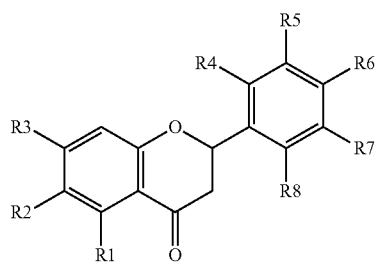

(1)

wherein

R1, R3 and R6 are each H or X—R9, wherein X is selected from —CH$_2$—, —O—, —S—, —NH—, —N=, —C(=O)— or —OC(=O)—; R9 is selected from H, C$_{1-12}$alkyl, C$_{2-12}$alkenyl or C$_{2-12}$alkynyl;

R2 is selected from C$_{1-12}$alkyl, C$_{2-12}$alkenyl or C$_{2-12}$alkynyl, wherein C$_{1-12}$alkyl, C$_{2-12}$alkenyl or C$_{2-12}$alkynyl is unsubstituted or substituted one or more C$_{1-6}$alkyl, OH, NH$_2$, CN, NO, CHO or halo;

R4 and R8 are each selected from H, C$_{1-12}$alkyl, C$_{2-12}$alkenyl or C$_{2-12}$alkynyl, wherein C$_{1-12}$alkyl, C$_{2-12}$alkenyl or C$_{2-12}$alkynyl is unsubstituted or substituted one or more C$_{1-6}$alkyl, OH, NH$_2$, CN, NO, CHO or halo;

R5 and R7 are each H, OH, C$_{1-12}$alkyl, C$_{2-12}$alkenyl or C$_{2-12}$alkynyl, wherein C$_{1-12}$alkyl, C$_{2-12}$alkenyl or C$_{2-12}$alkynyl is unsubstituted or substituted one or more C$_{1-6}$alkyl, OH, NH$_2$, CN, NO, CHO or halo;

or a pharmaceutically acceptable salt.

In one embodiment of the present invention, the compound of formula (1) has the following structure:

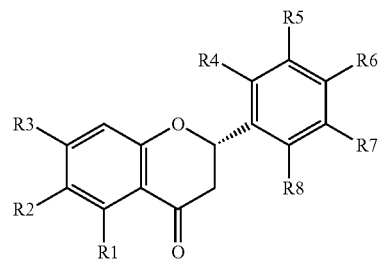

wherein R1 to R8 are defined as above.

In one embodiment of the present invention, R1, R3 and R6 are each preferably selected from H, OH, OCH$_3$ or OCH$_2$CH$_3$.

In one embodiment of the present invention, R2 is preferably selected from H,

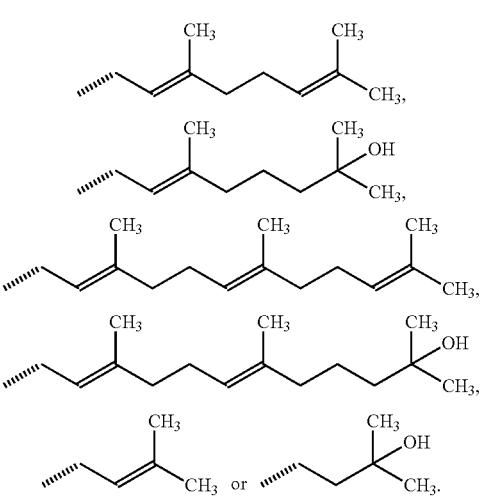

In one embodiment of the present invention, R4 and R8 are each preferably selected from H,

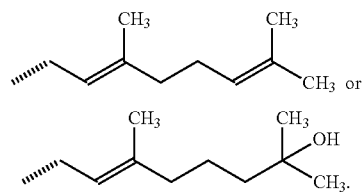

or

In one embodiment of the present invention, R5 and R7 are each preferably selected from H, OH,

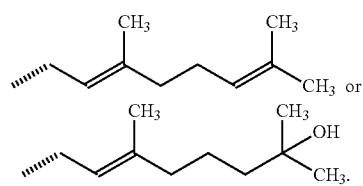

or

In one preferable embodiment of the present invention, the compound of formula (1) is as follows:

(S,E)-2-(3,4-dihydroxyphenyl)-6-(3,7-dimethylocta-2,6-dien-1-yl)-5,7-dihydroxy-3,4-dihydro-2H-1-benzopyran-4-one (PPC)

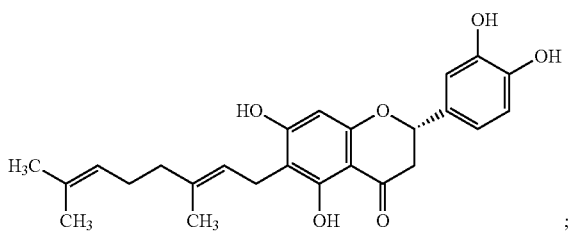

(PPC)

(S,E)-2-(2-(3,7-dimethylocta-2,6-dien-1-yl)-3,4-dihydroxyphenyl)-5,7-dihydroxy-3,4-dihydro-2H-1-benzopyran-4-one (PPD)

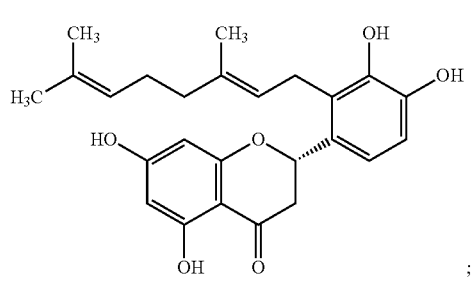

(PPD)

(S,E)-2-(3-(3,7-dimethylocta-2,6-dien-1-yl)-4,5-dihydroxyphenyl)-5,7-dihydroxy-3,4-dihydro-2H-1-benzopyran-4-one (PPF)

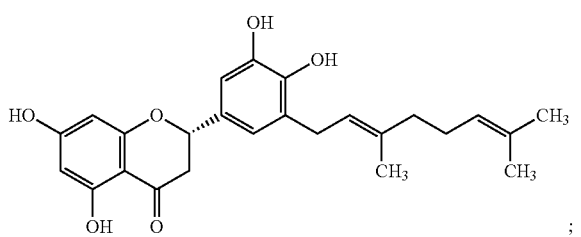

(PPF)

(S,E)-2-(2-(3,7-dimethylocta-2,6-dien-1-yl)-3,4-dihydroxyphenyl)-5,7-dihydroxy-6-(3-methylbut-2-en-1-yl)-3,4-dihydro-2H-1-benzopyran-4-one (PPG)

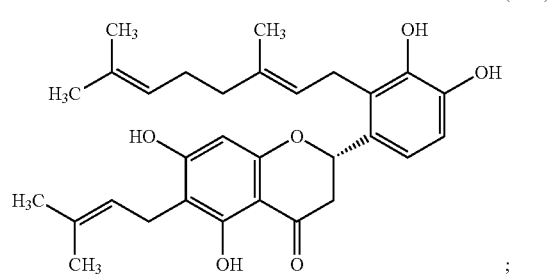

(PPG)

(S,E)-2-(3-(3,7-dimethylocta-2,6-dien-1-yl)-4-hydroxyphenyl)-5,7-dihydroxy-3,4-dihydro-2H-1-benzopyran-4-one (PPH)

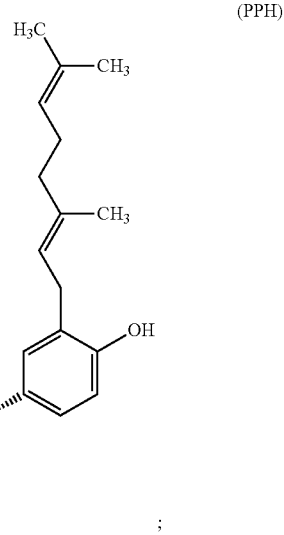

(PPH)

(S)-2-(3,4-dihydroxyphenyl)-5,7-dihydroxy-6-((2E,6E)-3,7,11-trimethyldodeca-2,6,10-trien-1-yl)-3,4-dihydro-2H-1-benzopyran-4-one (PPI)

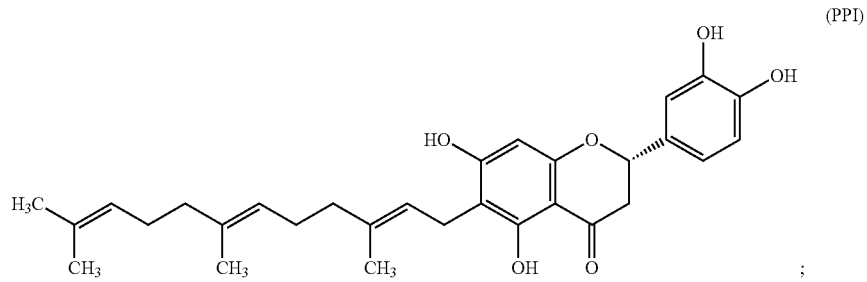 [SMILES: CC(C)=CCC/C(C)=C/CC/C(C)=C/Cc1c(O)cc2c(c1O)C(=O)C[C@@H](c1ccc(O)c(O)c1)O2]

(S,E)-6-(3,7-dimethylocta-2,6-dien-1-yl)-5,7-dihydroxy-2-(4-hydroxyphenyl)-3,4-dihydro-2H-1-benzopyran-4-one (PPJ)

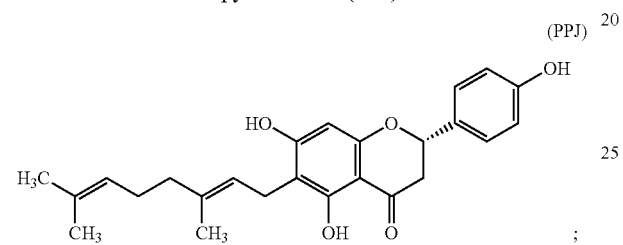

(S,E)-2-(3,4-dihydroxy-2-(7-hydroxy-3,7-dimethyloct-2-en-1-yl)phenyl)-5,7-dihydroxy-3,4-dihydro-2H-1-benzopyran-4-one (PPA)

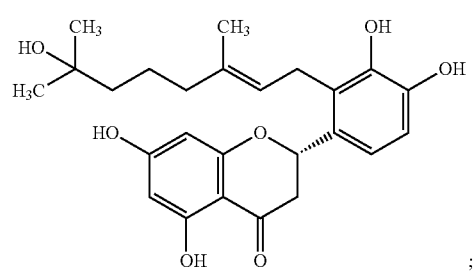

(S,E)-2-(3,4-dihydroxy-5-(7-hydroxy-3,7-dimethyloct-2-en-1-yl)phenyl)-5,7-dihydroxy-3,4-dihydro-2H-1-benzopyran-4-one (PPB)

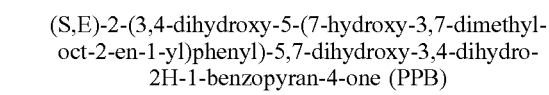

(S,E)-2-(3,4-dihydroxyphenyl)-5,7-dihydroxy-6-(7-hydroxy-3,7-dimethyloct-2-en-1-yl)-3,4-dihydro-2H-1-benzopyran-4-one (Pokinawan)

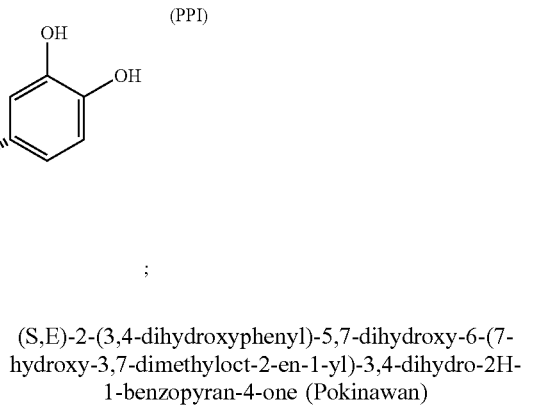

(S,E)-5,7-dihydroxy-2-(4-hydroxy-3-(7-hydroxy-3,7-dimethyloct-2-en-1-yl)phenyl)-3,4-dihydro-2H-1-benzopyran-4-one (PPE)

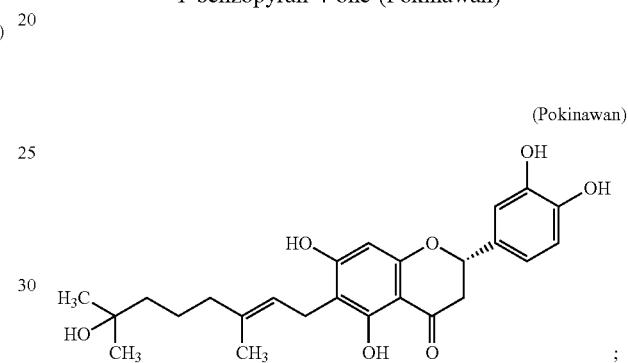

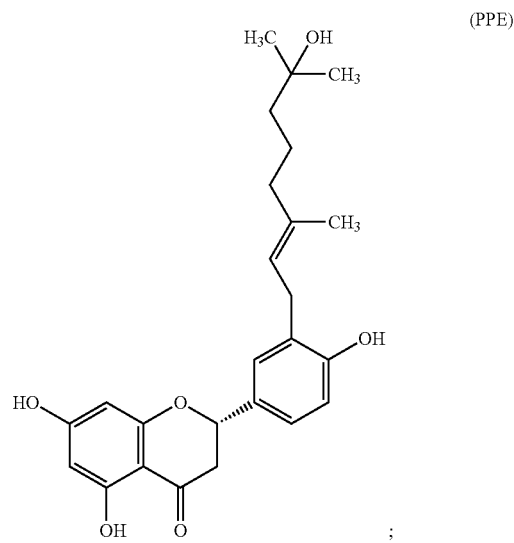 [SMILES: C/C(=C\Cc1cc([C@@H]2CC(=O)c3c(O)cc(O)cc3O2)ccc1O)CCCC(C)(C)O]

(S,E)-2-(3,4-dihydroxy-2-(7-hydroxy-3,7-dimethyl-oct-2-en-1-yl)phenyl)-5,7-dihydroxy-6-(3-hydroxy-3-methylbutyl)-3,4-dihydro-2H-1-benzopyran-4-one

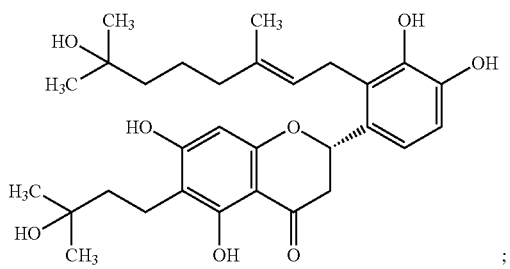 [SMILES: C/C(=C\Cc1c([C@@H]2CC(=O)c3c(cc(O)c(CCC(C)(C)O)c3O)O2)ccc(O)c1O)CCCC(C)(C)O]

(S)-2-(3,4-dihydroxyphenyl)-5,7-dihydroxy-6-((2E,6E)-11-hydroxy-3,7,11-trimethyldodeca-2,6-dien-1-yl)-3,4-dihydro-2H-1-benzopyran-4-one

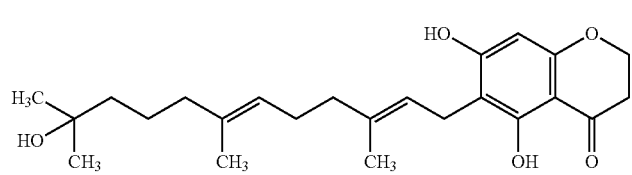

or (S,E)-5,7-dihydroxy-6-(7-hydroxy-3,7-dimethyloct-2-en-1-yl)-2-(4-hydroxyphenyl)-3,4-dihydro-2H-1-benzopyran-4-one

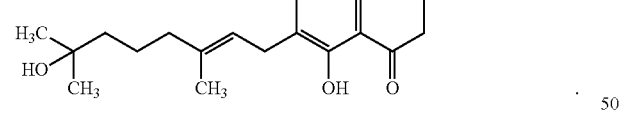

In one embodiment of the present invention, the compound of formula (1) can be used in preparation of a composition for treating or preventing diabetes. In one preferable embodiment of the present invention, the compound of formula (1) can be used in preparation of a composition for treating or preventing type II diabetes.

Another purpose of the present invention is to provide a composition for the treatment or prevention of diabetes, comprising the compound of formula (1) as mentioned above.

Another purpose of the present invention is to provide a novel use of Taiwan Green Propolis or an extract thereof in the preparation of a composition for modulating blood glucose, preferably for the treatment or prevention of diabetes, more preferably for the treatment or prevention of type II diabetes.

According to the present invention, the composition for modulating blood glucose may be used as drugs, health food or food supplements.

According to the present invention, Taiwan Green Propolis or an extract thereof includes at least one of the following compounds:

(S,E)-2-(3,4-dihydroxyphenyl)-6-(3,7-dimethylocta-2,6-dien-1-yl)-5,7-dihydroxy-3,4-dihydro-2H-1-benzopyran-4-one (PPC)

(PPC)

![PPC structure]

(S,E)-2-(2-(3,7-dimethylocta-2,6-dien-1-yl)-3,4-dihydroxyphenyl)-5,7-dihydroxy-3,4-dihydro-2H-1-benzopyran-4-one (PPD)

(PPD)

![PPD structure]

(S,E)-2-(3-(3,7-dimethylocta-2,6-dien-1-yl)-4,5-dihydroxyphenyl)-5,7-dihydroxy-3,4-dihydro-2H-1-benzopyran-4-one (PPF)

(PPF)

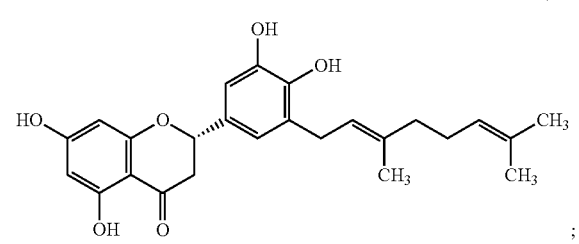

(S,E)-2-(2-(3,7-dimethylocta-2,6-dien-1-yl)-3,4-dihydroxyphenyl)-5,7-dihydroxy-6-(3-methylbut-2-en-1-yl)-3,4-dihydro-2H-1-benzopyran-4-one (PPG)

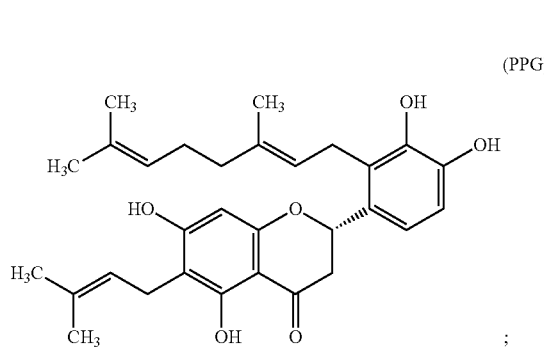
(PPG)

(S,E)-2-(3-(3,7-dimethylocta-2,6-dien-1-yl)-4-hydroxyphenyl)-5,7-dihydroxy-3,4-dihydro-2H-1-benzopyran-4-one (PPH)

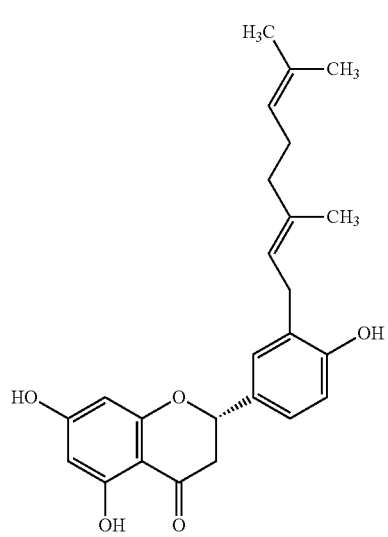
(PPH)

(S)-2-(3,4-dihydroxyphenyl)-5,7-dihydroxy-6-((2E,6E)-3,7,11-trimethyldodeca-2,6,10-trien-1-yl)-3,4-dihydro-2H-1-benzopyran-4-one (PPI)

(S,E)-6-(3,7-dimethylocta-2,6-dien-1-yl)-5,7-dihydroxy-2-(4-hydroxyphenyl)-3,4-dihydro-2H-1-benzopyran-4-one (PPJ)

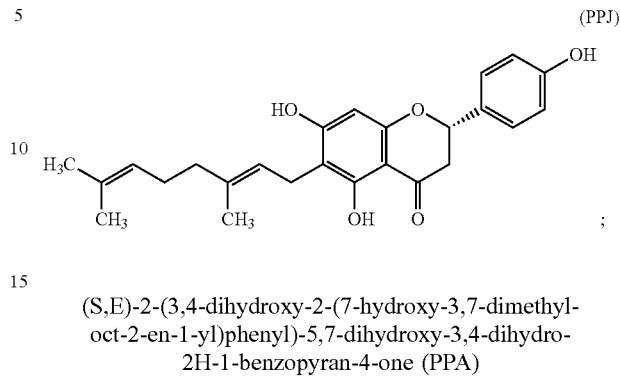
(PPJ)

(S,E)-2-(3,4-dihydroxy-2-(7-hydroxy-3,7-dimethyloct-2-en-1-yl)phenyl)-5,7-dihydroxy-3,4-dihydro-2H-1-benzopyran-4-one (PPA)

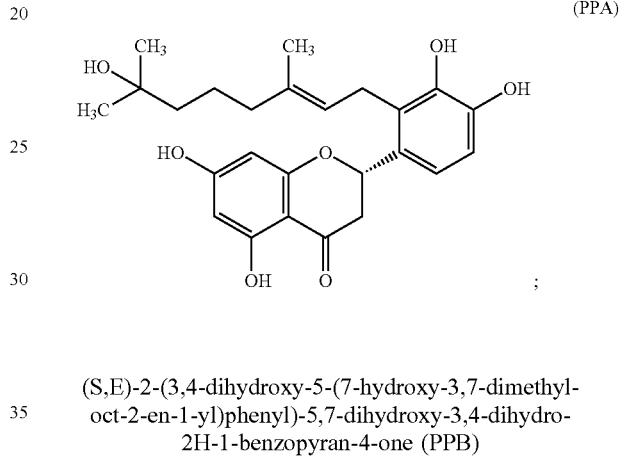
(PPA)

(S,E)-2-(3,4-dihydroxy-5-(7-hydroxy-3,7-dimethyloct-2-en-1-yl)phenyl)-5,7-dihydroxy-3,4-dihydro-2H-1-benzopyran-4-one (PPB)

(PPB)

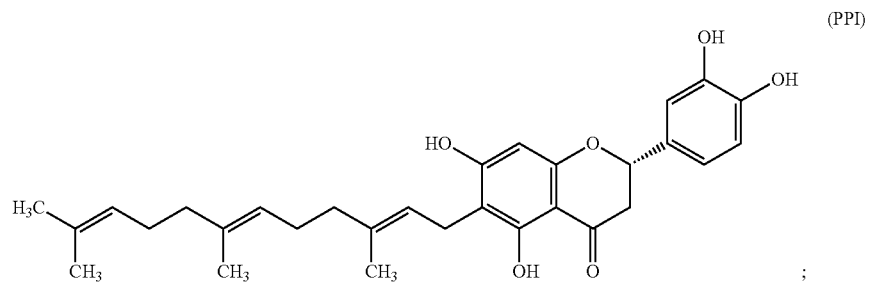 [SMILES: CC(C)=CCC/C(C)=C/CC/C(C)=C/Cc1c(O)cc2c(c1O)C(=O)C[C@@H](c1ccc(O)c(O)c1)O2]
(PPI)

(S,E)-5,7-dihydroxy-2-(4-hydroxy-3-(7-hydroxy-3,
7-dimethyloct-2-en-1-yl)phenyl)-3,4-dihydro-2H-1-
benzopyran-4-one (PPE)

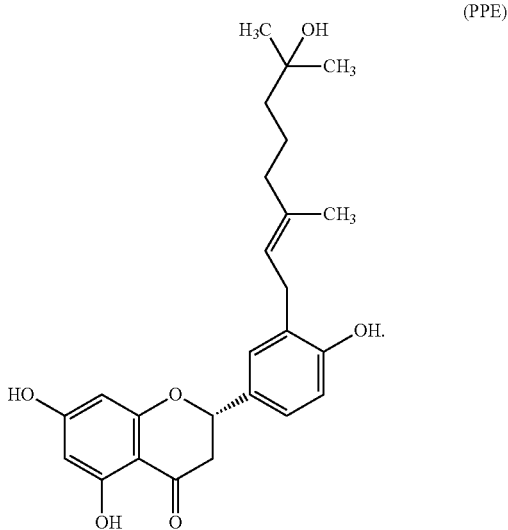 [SMILES: C/C(=C\Cc1cc([C@@H]2CC(=O)c3c(O)cc(O)cc3O2)ccc1O)CCCC(C)(C)O]

(PPE)

EXAMPLES

Any and all of the embodiments herein are intended for full illustration of the present invention only and do not impose limitation on a scope of the present invention.

In one embodiment of the present invention, a compound used as a novel medicament for modulation of blood glucose is extracted from Taiwan Green Propolis. It was found from analysis that the resulting extract has the principal components of PPA to PPJ and derivatives thereof.

Materials and Method

Preparation of Taiwan Green Propolis Alcohol Extract (TPE)

About 2 kg of Taiwan Green Propolis was collected from a bee farm in Tainan, Taiwan, in July 2010. The Taiwan Green Propolis was dewaxed and then extracted with 95% alcohol for about 3 weeks. After the filtration of alcohol and the removal of impurities, the liquid extract was concentrated under reduced pressure to obtain the Taiwan Green Propolis extract, which was placed into a refrigerator at −20° C. until use in the next step. The level of the active compounds in the extract was identified by HPLC analysis.

HPLC Analysis of Taiwan Green Propolis Alcohol Extract

The Taiwan Green Propolis alcohol extract was analyzed for composition and level of propolins by high performance liquid chromatography (HPLC). Luna Phenomenex C18 column (C18, 250×4.6 mm) was used for reverse chromatography. An 85:15 (v/v) ratio of methanol to water was used as a mobile phase, with a flow rate of 1.0 ml/min. A detector for an ultraviolet lamp has a wavelength of 280 nm. A load of a sample was 20 μL.

Chemical Composition for the Taiwan Green Propolis Alcohol Extract

The Taiwan Green Propolis alcohol extract has propolins as principal components, wherein PPC is a main component with the highest content, and the others such as PPD, PPF, PPG and PPH remain high. FIG. 1 is a diagram of HPLC analysis of the Taiwan Green Propolis alcohol extract and clearly illustrates the retention time and content of the ten compounds of PPA to PPJ in the Taiwan Green Propolis alcohol extract.

Inducing Mice with Diabetes

The male FBV mice of 5 weeks old, commercially available from BioLASCO Co., Ilan, Taiwan, were acclimatized for 1 week, prior to administration of streptozotocin (STZ) at 40 mg/kg for 3 consecutive days. STZ was formulated with an aqueous solution of sodium citrate (pH 4.5, 73.5 mg/5 mL) on ice, and then 100 μL of the formulation was dosed by intraperitoneal injection. From day 2 in the 3 consecutive days, the mice were dosed with 5% (w/v) glucose water for 6 consecutive days. After allowing the mice to rest for 10 days, blood glucose levels were measured. After administration of STZ for 1 week, about 5 μL of blood was collected from each of the mice at the tail vein, and was assayed for blood glucose by a blood glucose monitor and chip (FORA, California, U.S.A.). After 1 week, blood glucose was detected once more, and whether blood glucose was smooth or not was evaluated prior to grouping. The values of blood glucose in all of the mice induced to suffer from diabetes were brought to fall within about 300±50 mg/dL.

Taiwan Green Propolis Alcohol Extract (TPE) Group

An appropriate amount of the Taiwan Green Propolis alcohol extract was dissolved with 3 ml 95% alcohol and then uniformly mixed with 80 μL Tween 80 as a cosolvent; after concentrating under reduced pressure for removal of alcohol, it was dispersed into 16 ml water to give a liquid mixture of the Taiwan Green Propolis extract. This mixture was fed by 200 μL gavage into the diabetic mice designated as the Taiwan Green Propolis extract group.

Propolins and its Relevant Derivatives Group

An appropriate amount of propolins and its relevant derivatives, such as PPA, PPB, PPC, PPD, PPE, PPF, PPG, PPH, PPI or PPJ, was dissolved with 3 ml 95% alcohol and then uniformly mixed with 80 μL Tween 80; after concentrating under reduced pressure for removal of alcohol, it was uniformly dispersed into 16 ml water to give a liquid mixture of propolins. This mixture was fed by 200 μL gavage into the diabetic mice designated as the propolins and its relevant derivative group.

DPP4 Inhibitor Group (DPP4I) (Januvia)

Sitagliptin (trade name: Januvia), commercially available from American Merck Co., was used as the DPP4 inhibitor. An appropriate amount of sitagliptin was dissolved in water to provide a final concentration allowing administration of the mice at a dose of 370 mg/kg. In the following example, Januvia was representative of the DPP4 inhibitors and acted as a positive control group for reference.

STZ Group (Comparison Group for the Mice Induced with Diabetes) and Control Group (Con)

Tween 80 (80 μL) was mixed into 16 ml water to give a placebo, which was fed by 200 μL gavage into the STZ-induced diabetic mice or normal mice (i.e., the mice without induction for diabetes). Oral gavage was carried out once at a fixed time each day, and weight, feedstuff intake and water intake were measured weekly until tests were finished at 12-13 weeks.

Oral Glucose Tolerance Test (OGTT)

After administration of the testing substance to the animals for 12 weeks, the OGTT test was performed for evaluation of secretion and effects of insulin. All of the mice in the test were administered with the testing substance and then fasted for 4 hours prior to blood sampling at the first point called point 0. Afterwards, the mice were fed by oral gavage with 200 μL glucose in water, equivalent to a dose of 1.0 g/kg. After administration, blood was collected for an assay of blood glucose at 15, 30, 60, 120 and 180 minutes, respectively. Therefore, a total of 6 points, including points at 0, 15, 30, 60, 120 and 180 minutes, were obtained. About 5 μL of blood was collected from each of the mice at the tail vein and was then assayed for blood glucose by the blood glucose monitor and chip (FORA, California, U.S.A.). The blood glucose values at the Y-axis were plotted against the time points at the X-axis. Each group was calculated for an area under curve for comparison. The efficacy in regulation of blood glucose was evaluated by the area showing a relationship between the testing substance and secretion and effects of insulin.

Analysis of Glycosylated Hemoglobin HbA1c

The glycosylated hemoglobin was used for evaluation of the efficacy of the testing substance in the regulation of blood glucose. After administration of the testing substance for 12 weeks, blood was collected for analysis of the glycosylated hemoglobin HbA1c. 500 μL blood collected from each of the mice was delivered to the Super Laboratory Co. (New Taipei City, Taiwan) for analysis. The analysis may confer an average and standard deviation to each group of the mice. In the event the presence of the blood glucose modulation efficacy for the testing substance, this value would be lower; and in the event the absence of the blood glucose modulation efficacy for the testing substance, this value would be higher.

Results

Effects of TPE on Weight of the Diabetic Mice

Following a recommendation from the literature, the diabetic mice of the DPP4I group were dosed at 370 mg/kg/mouse, and this dose was converted to a dose of 2,466.7 mg/day for administration to an adult human of 60 kg. For the diabetic patients, Januvia was recommended to use once daily, 100 mg given for each time. In the following example, Januvia was used at a dose of about 25 times higher than the recommended dosage for a normal human body, thus enabling control of blood glucose in the diabetic mice. In the following example, the Januvia group was used as positive control group for comparison; the healthy mice without induction of STZ were used as a negative control group; the STZ-induced diabetic mice were used as a control group, wherein in these control groups, of the drug or testing substance was not used, i.e., only the placebo was administered. In one example of the present invention, the daily dose for the Taiwan Green Propolis alcohol extract group (TPE) was 36 mg/kg/mouse, equivalent to a dose of 240 mg/day for the adult human of 60 kg.

Figure 2:
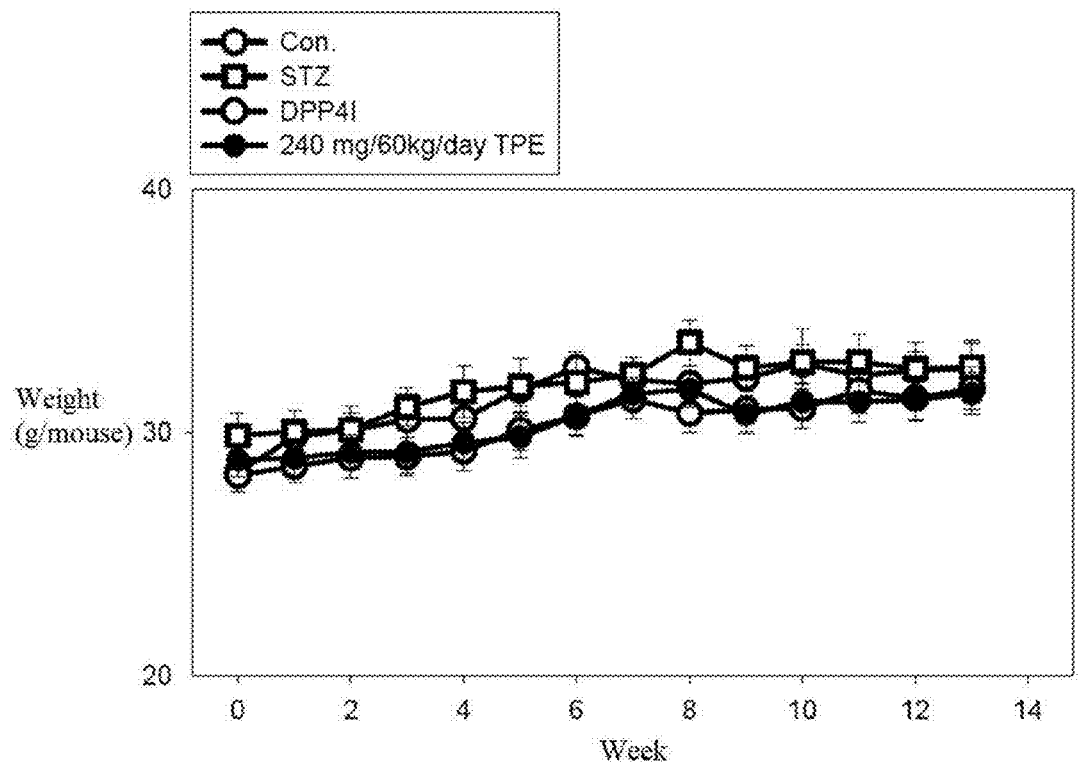
FIG. 2 shows the variation of weight of the mice after administration of TPE.

FIG. 2 shows the variation of weight of the mice after administration of TPE. After administration for 13 weeks, there was no significant alteration in weight of the mice in all of the groups.

Effects of TPE on Blood Glucose in the Diabetic Mice

For the 7 diabetic mice in each group, the Taiwan Green Propolis extract (TPE) was administered orally at a dose of 36 mg/kg/day when the blood glucose value was about 350 mg/dL. After calculation, this dose is equivalent to a dose of 240 mg/day for an adult human of 60 kg. Oral administration was carried out once at a fixed time each day, and weight, feedstuff intake, water intake and blood glucose were measured weekly, with administration for a total of 13 weeks. Following recommendation in the literature, Januvia used in the positive control group was orally administered to the mice at a dose of 370 mg/kg. After calculation, this dose is equivalent to a dose of 2,467 mg/day for an adult human of 60 kg. The mice without induction of STZ were used as the negative control group, while the STZ-induced diabetic mice were used as the control group.

Figure 3:
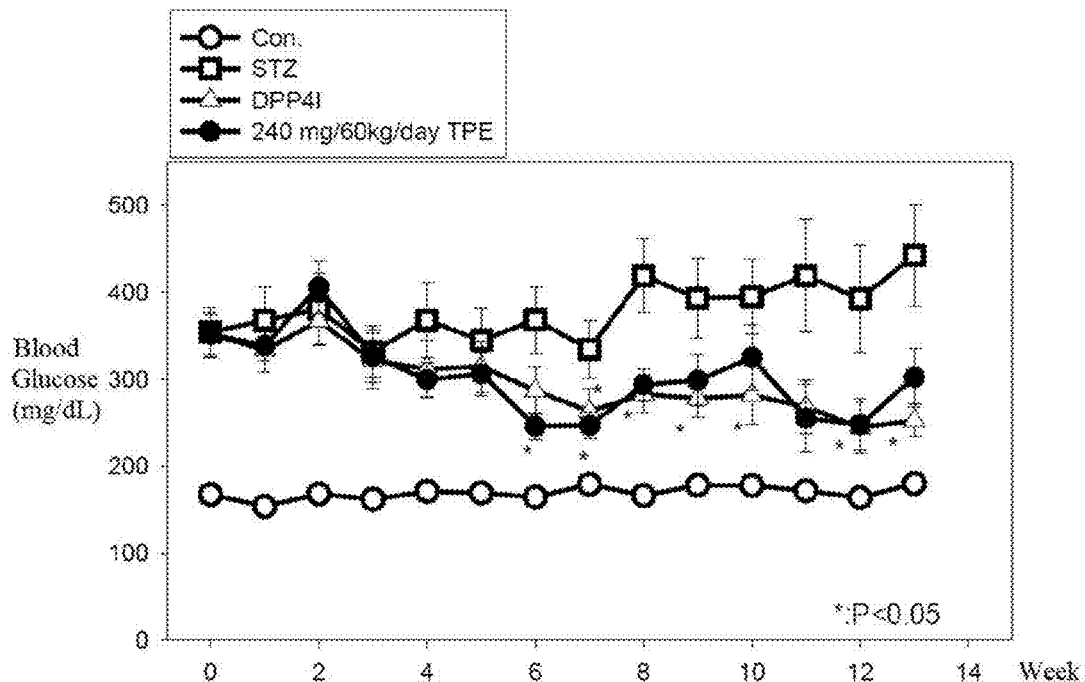
FIG. 3 shows the variation of blood glucose in the mice after administration of TPE.

FIG. 3 shows the variation of blood glucose in the mice after administration of TPE. After administration for 13 weeks, blood glucose was significantly modulated by TPE. After administration for 6-7 weeks, the efficacy of TPE for modulation of blood glucose was significant and equivalent to the efficacy of Januvia for the modulation of blood glucose. In the negative control group (normal healthy mice), the blood glucose value was kept smoothly at about 180 mg/dL. In the control group, the blood glucose value was increased from 350 mg/dL to 470 mg/dL. From the test results, it can be clearly observed that the efficacy of TPE for the modulation of blood glucose is significant.

Effects of TPE on Feedstuff Intake of the Diabetic Mice

Figure 4:
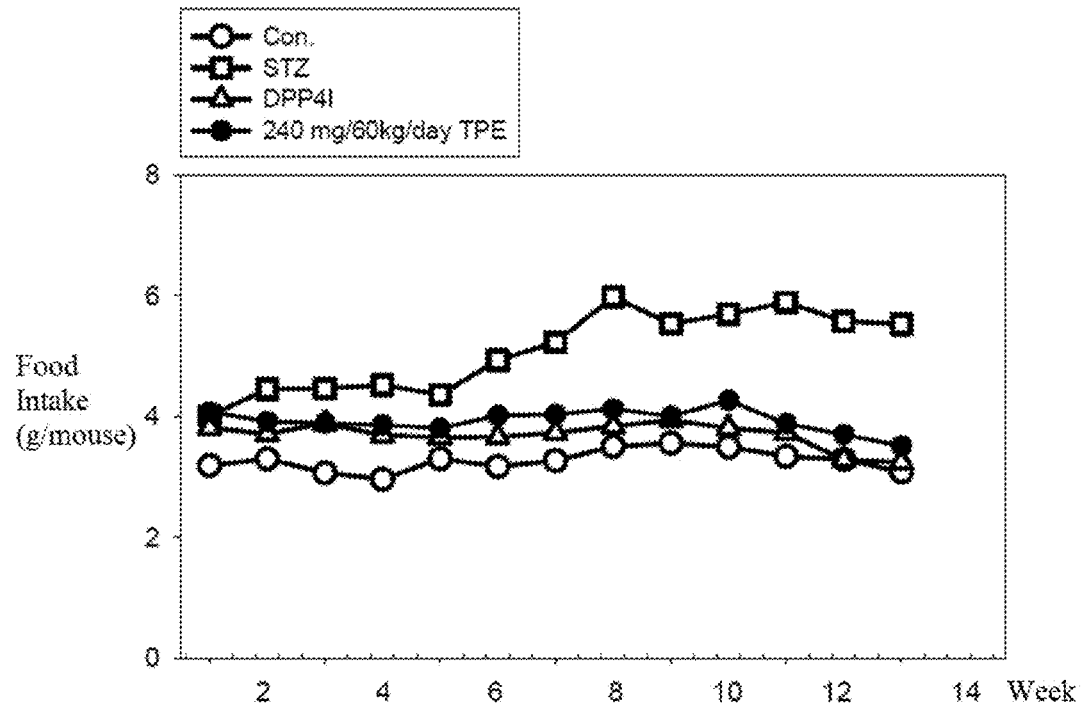
FIG. 4 shows the variation of food intake of the mice after administration of TPE.

FIG. 4 shows variation of food intake of the mice after administration of TPE. In the mice of TPE group, the initial intake of feedstuff was about 4.0 g/day/mouse. After administration of TPE for 13 weeks, food intake was reduced to be about 3.5 g/day/mouse. Similarly, the test results were the same as in the Januvia group. In contrast to the STZ group, after administration of the placebo for 8 weeks, the food intake was increased from the original 4.0 g/day/mouse to 6.0 g/day/mouse; and after administration for 13 weeks, food intake still remained 5.7 g/day/mouse. In the negative control group, the food intake was about 3.2-3.5 g/day/mouse. From the test results, it is clear that TPE according to the present invention had the similar efficacy as Januvia and may be effective for the reduction of food intake of the diabetic mice. As shown in FIG. 1, during administration of TPE, the mice in the TPE group were the same as the STZ group in variation of weight but were distinct in feedstuff intake. This indicates that TPE and Januvia have the efficacy for modulation of blood glucose, enabling preferable utilization of the intake food energy.

Effects of TPE on Water Intake of the Diabetic Mice

Figure 5:
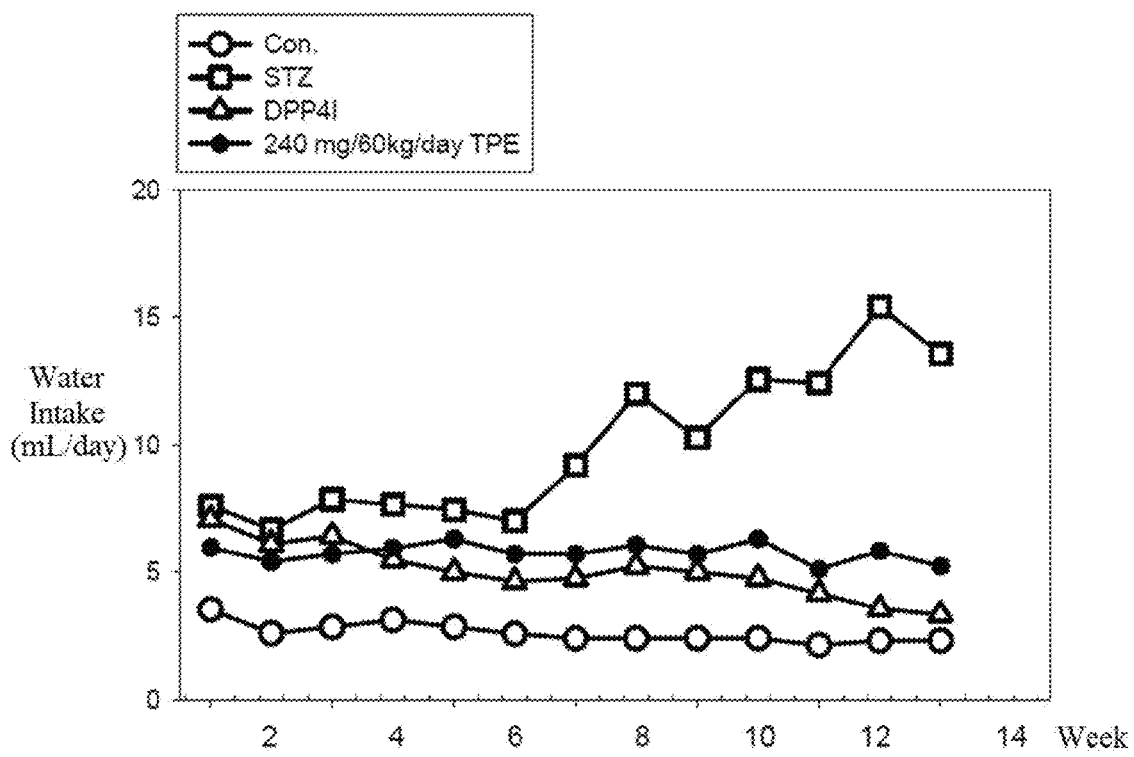
FIG. 5 shows the variation of water intake of the mice after administration of TPE.

FIG. 5 shows the variation of water intake of the mice after administration of TPE. In the STZ group, after administration of the placebo for 8 weeks, water intake was increased from 7.5 mL/day/mouse in the first week to 12.5 mL/day/mouse. During this time, water intake was increased from 5.8 mL/day/mouse in the first week to 6.0 mL/day/mouse for the mice in the TPE group and was reduced from 7.0 mL/day/mouse in the first week to 5.4 mL/day/mouse for the mice in the Januvia group.

In the STZ group, after administration of the placebo for 13 weeks, water intake was increased from 7.5 mL/day/mouse in the first week to 13.8 mL/day/mouse. During this time, water intake was increased from 5.8 mL/day/mouse in the first week to 5.3 mL/day/mouse for the mice in the TPE group and was reduced from 7.0 mL/day/mouse in the first week to 3.8 mL/day/mouse for the mice in the Januvia group. From the test results, it is observed that Taiwan Green Propolis enables significant reduction of water intake of the diabetic mice, thus having the efficacy for treatment of diabetes.

Efficacy of TPE in the Glucose Tolerance Test

Figure 6:
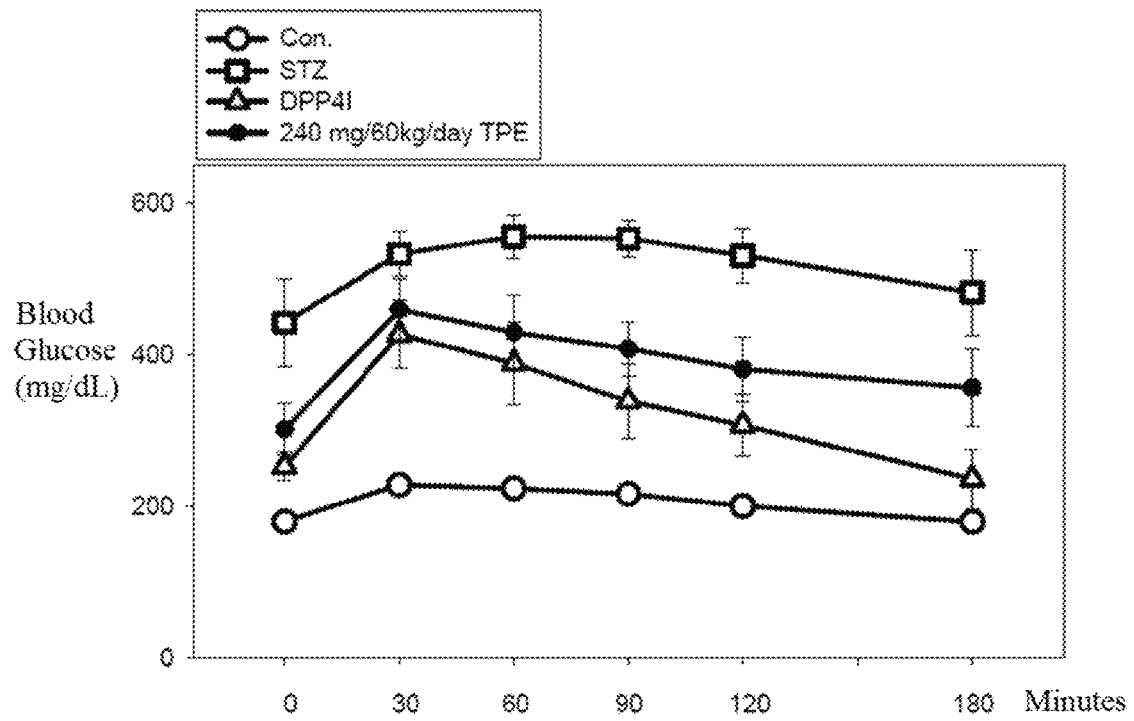
FIG. 6 shows the variation of blood glucose in the mice after administration of TPE.

FIG. 6 shows the variation of blood glucose in the mice after administration of TPE in the glucose tolerance test. In the STZ group, the blood glucose value of the mice was about 450 mg/dL at 0 point; about 540 mg/dL at the 30-minute time point after administration of glucose in water; peaked to about 560 mg/dL at the 60- to 90-minute time points; and returned to 490 mg/dL at the 180-minute time point. In the TPE group, the blood glucose value of the mice was about 300 mg/dL at 0 point; about 460 mg/dL at the 30-minute time point after administration of glucose in water; about 430-405 mg/dL at the 60- to 90-minute time points; and returned to 360 mg/dL at the 180-minute time point. In the Januvia group, the blood glucose value of the mice was about 260 mg/dL at 0 point; peaked to about 420 mg/dL at the 30-minute time point after administration of glucose in water; about 390-340 mg/dL at the 60- to 90-minute time points; and returned to 240 mg/dL at the 180-minute time point. In the negative control group, the blood glucose value of the mice was about 190 mg/dL at 0 point; peaked to about 230 mg/dL at the 30-minute time point after administration of glucose in water; about 220-215 mg/dL at the 60- to 90-minute time points; and returned to 190 mg/dL at the 180-minute time point. From the test results, it is clearly observed that TPE enables blood glucose to significantly return to its normal level.

Figure 7:
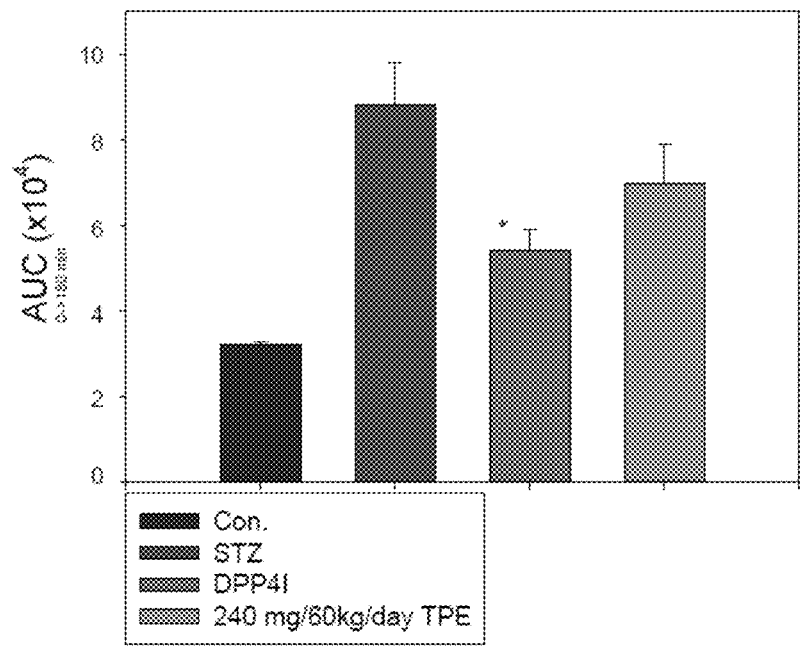
FIG. 7 shows an AUC graph of blood glucose in the mice after administration of TPE.

FIG. 7 shows an AUC graph of blood glucose in the mice after administration of TPE, with time at the X-axis versus the blood glucose value at the Y-axis, analyzed by the sigma plot software and calculated in integral area. As shown in FIG. 7, since the functions as insulin secretion from the beta cells are normal in the mice of the negative control group, it has a minimal integral area with an AUC value of about $3.8 \times 10^4$; since the beta cells are damaged and insulin secretion is less in the mice of the STZ group, it has a maximal integral area with an AUC value of about $9.7 \times 10^4$; since a part of the functions of the beta cells are restored and basic insulin secretion is maintained in the mice of the DPP4I group, it has a significantly reduced integral area with an AUC value of about $5.8 \times 10^4$, when compared to the STZ group; and similarly, TPE has the similar efficacy as DPP4I, which enables partial restoration of functions of the beta cells and maintenance of basic insulin secretion, and enables significant reduction of the integral area with an AUC value of about $7.2 \times 10^4$ when compared to the STZ group. In case of respective comparison between the STZ group and the DPP4I group or the TPE group, DPP4I and TPE enable reduction of 66.1% and 42.4%, respectively. From the test results, it is clearly observed that TPE indeed has the efficacy for modulation of blood glucose.

Effects of TPE on Glycosylated Hemoglobin

Figure 8:
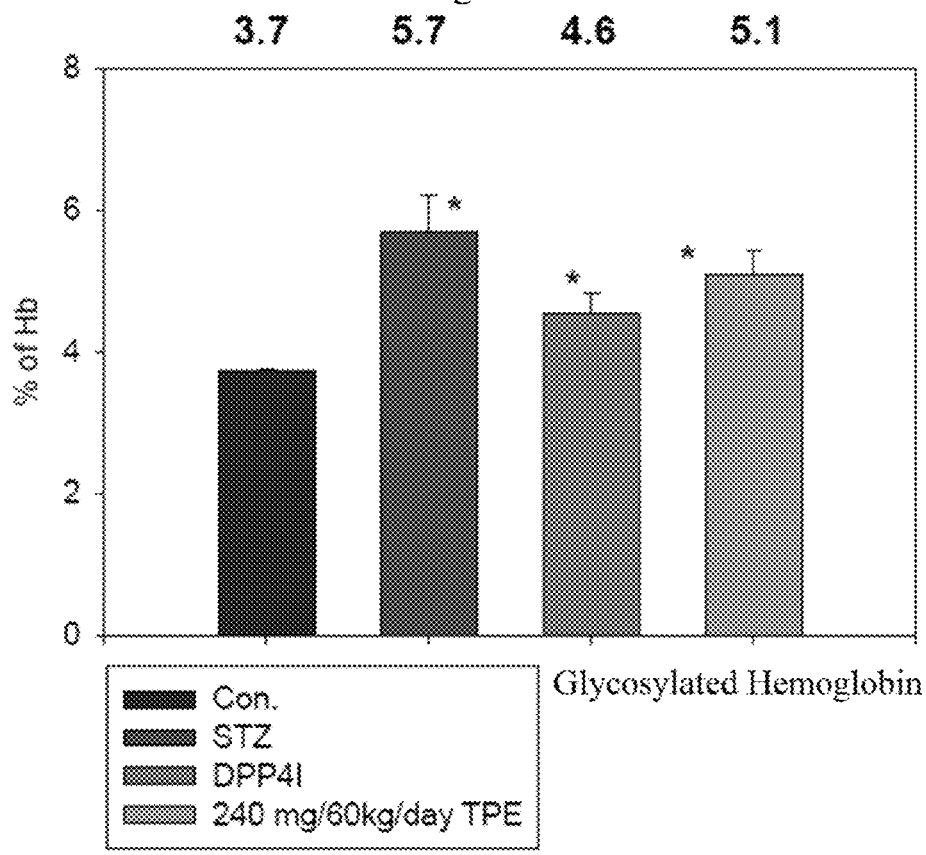
FIG. 8 shows the data of glycosylated hemoglobin in the mice after administration of TPE.
Figure 9:
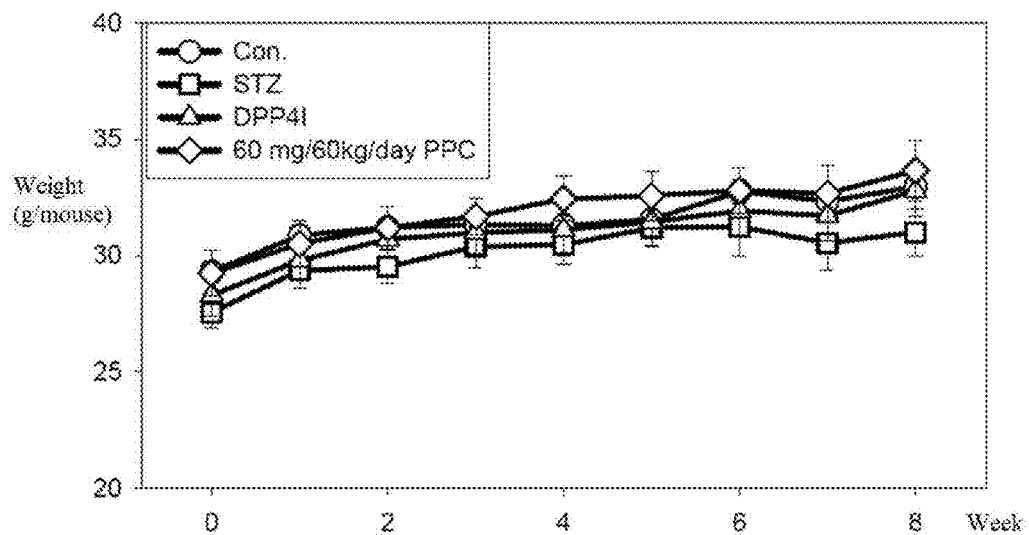
FIG. 9 shows the variation of weight of the mice after administration of PPC.
Figure 10:
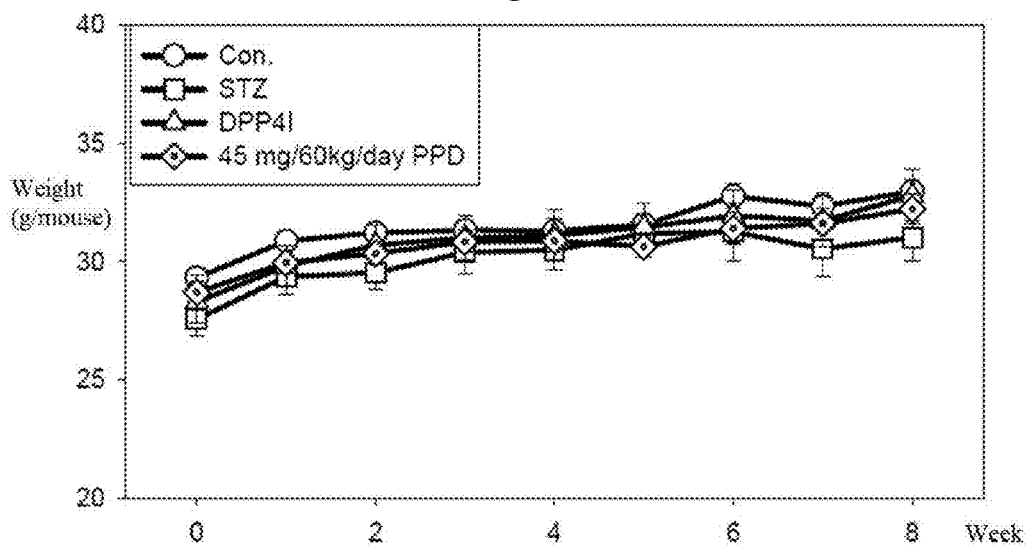
FIG. 10 shows the variation of weight of the mice after administration of PPD.
Figure 11:
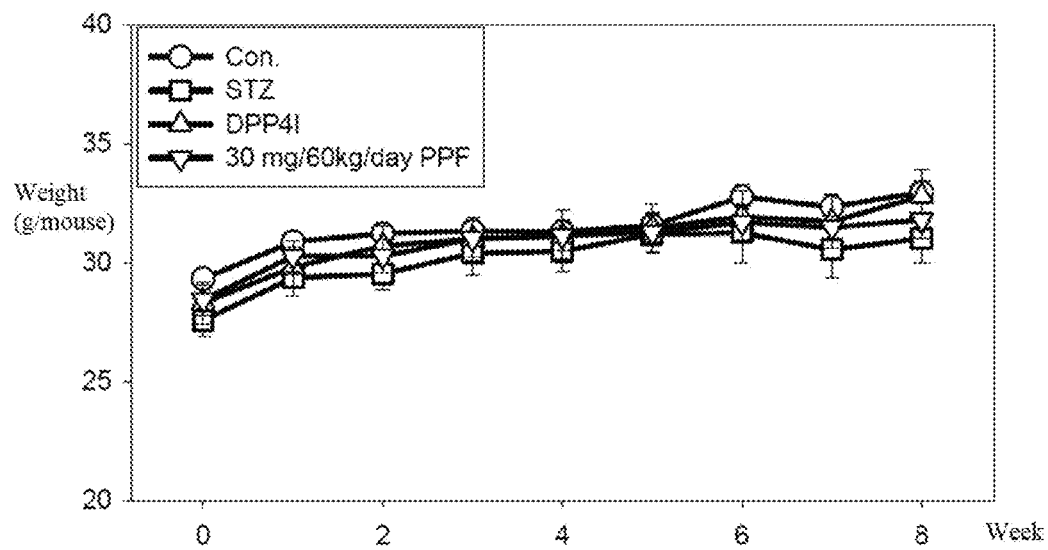
FIG. 11 shows the variation of weight of the mice after administration of PPF.
Figure 12:
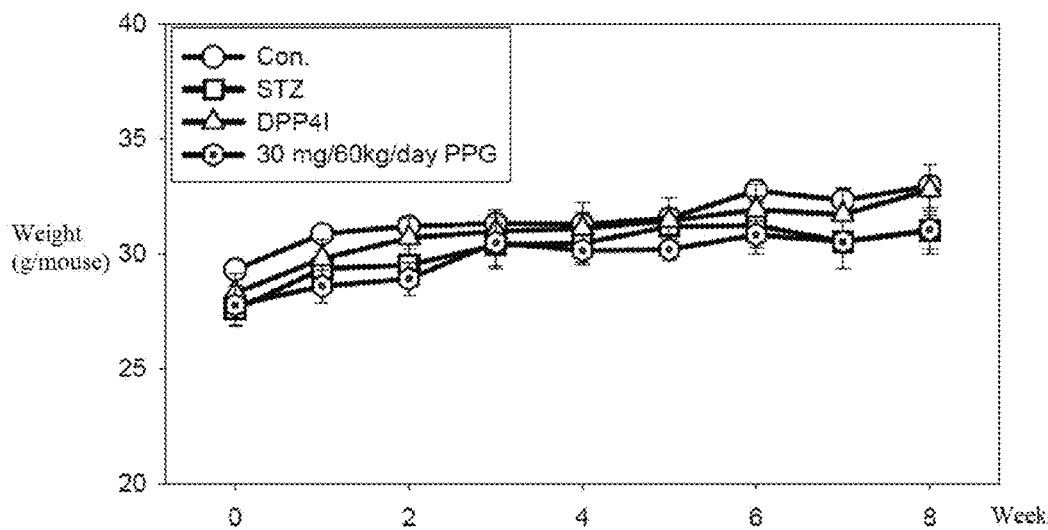
FIG. 12 shows the variation of weight of the mice after administration of PPG.

FIG. 8 shows the data of glycosylated hemoglobin in the mice after administration of TPE. As shown in FIG. 8, after respective administration of placebo or testing substance for 13 weeks, the value of glycosylated hemoglobin was about 5.7% in the mice of the STZ group, and about 3.7% in the negative control group, about 4.6% in the DPP4I group, and about 5.1% in the TPE group. From the test results, it is clearly observed that DPP4I is effective in reducing the generation of glycosylated hemoglobin by 55%. Where the dose of TPE (36 mg/kg) was that of DPP4I of 9.7% (370 mg/kg) only, TPE was also able to reduce the generation of glycosylated hemoglobin by 30%. Therefore, TPE according to the present invention has excellent effects for the reduction of glycosylated hemoglobin.

Effects of PPC, PPD, PPF and PPG on Weight of the Diabetic Mice

In the following example, on a basis of the content of propolins in Taiwan Green Propolis, 4 components, such as PPC, PPD, PPF and PPG, were selected for testing in the diabetic mice. In addition, on a basis of the doses corresponding to the dose of TPE administered (36 mg/kg/mouse), it was respectively converted to give the PPC dose of 9.0 mg/kg/mouse, equivalent to the dose of 60 mg/day for an adult human of 60 kg; to give the PPD dose of 6.75 mg/kg/mouse, equivalent to the dose of 45 mg/day for an adult human of 60 kg; to give the PPF dose of 4.5 mg/kg/mouse, equivalent to the dose of 30 mg/day for an adult human of 60 kg; and to give the PPG dose of 4.5 mg/kg/mouse, equivalent to the dose of 30 mg/day for an adult human of 60 kg. Following recommendation in the literature, the dose of DPP4I (Januvia) administered was 370 mg/kg/mouse. FIGS. 9 to 12 show a variation of weight of the mice after administration of PPC, PPD, PPF and PPG. After administration for 8 weeks, there was no significant variation in weight of the mice in the PPC, PPD, PPF and PPG groups, the negative control group, the control group and the positive control group.

Effects of PPC on Blood Glucose in the Diabetic Mice

Figure 13:
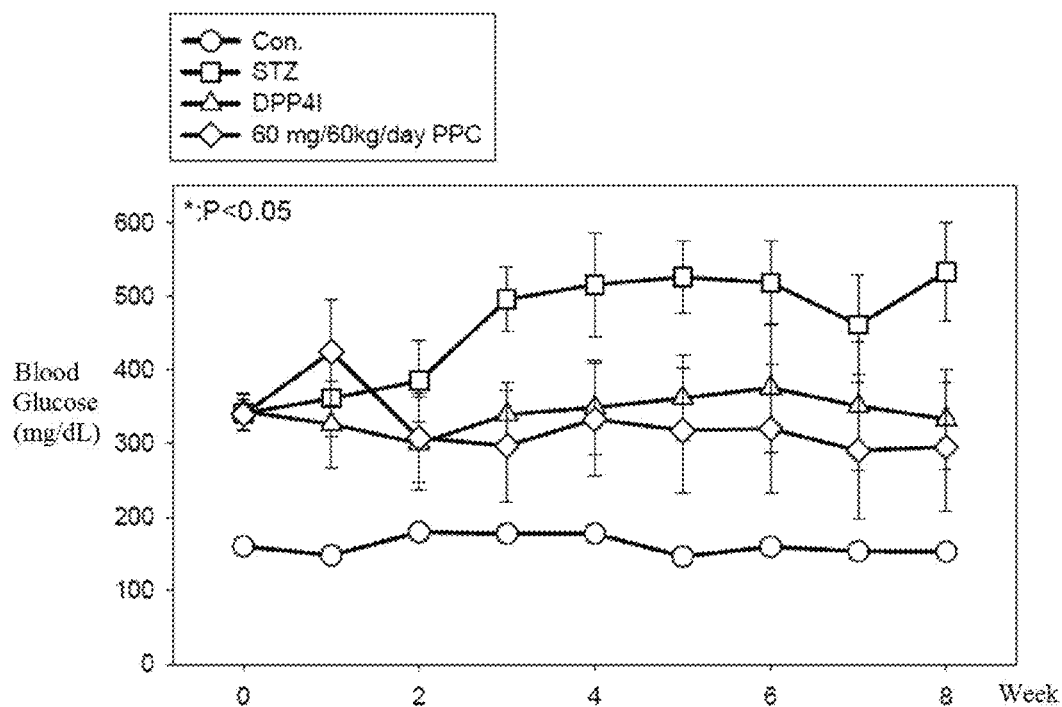
FIG. 13 shows the variation of blood glucose in the mice after administration of PPC.

The dose of PPC administered was 9.0 mg/kg/mouse, equivalent to the dose of 60 mg/day for an adult human of 60 kg. PPC was administered by gavage to the mice at the fixed time of every day, for total of 8 weeks. FIG. 13 shows variation of blood glucose in the mice after administration of PPC. As shown in FIG. 13, the value of blood glucose in the mice of the STZ group was increased from 330 mg/dL at 0 week to 530 mg/dL at 8 weeks; and after administration of Januvia for 8 weeks, the value of blood glucose in the mice of the DPP4I group was maintained effectively at 330 mg/dL. After administration of PPC for 8 weeks, blood glucose in the mice was reduced slightly from 330 mg/dL at 0 week to 298 mg/dL. In the negative control group, blood glucose in the mice was maintained stably at 180 mg/dL. From the test results, it is clearly observed that when the dose of PPC used is 2.4% of the Januvia dose, blood glucose is highly effectively modulated.

Effects of PPD on Blood Glucose in the Diabetic Mice

Figure 14:
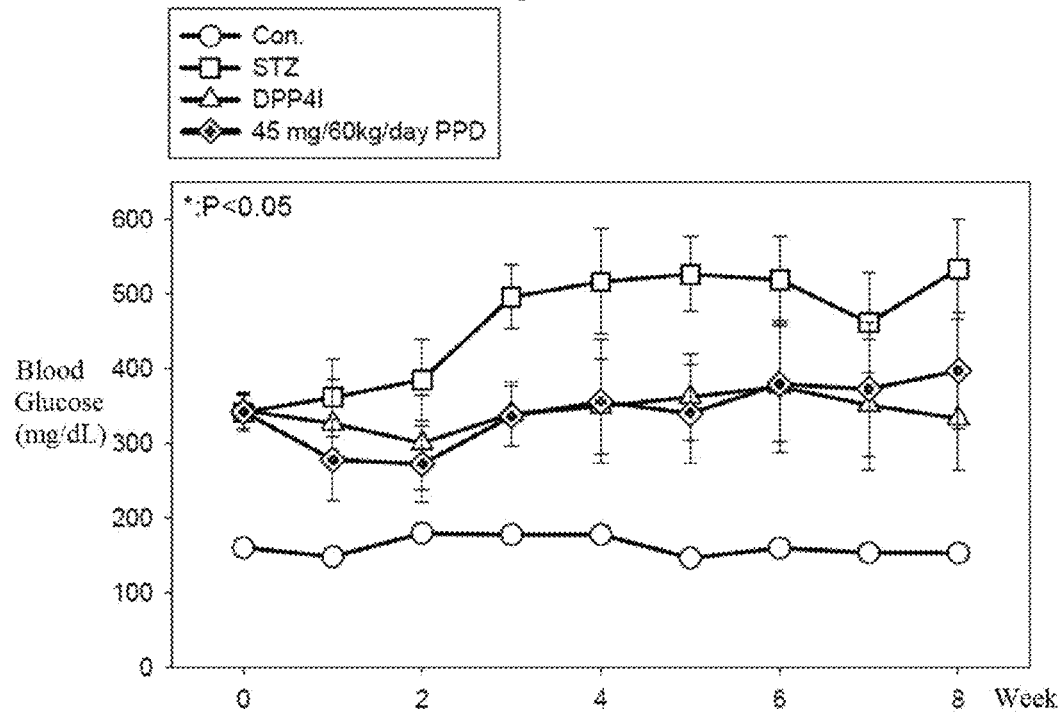
FIG. 14 shows the variation of blood glucose in the mice after administration of PPD.

The dose of PPD administered was 6.75 mg/kg/mouse, equivalent to the dose of 45 mg/day for an adult human of 60 kg. PPC was administered by gavage to the mice at the fixed time of every day, for total of 8 weeks. FIG. 14 shows variation of blood glucose in the mice after administration of PPD. As shown in FIG. 14, the value of blood glucose in the mice of the STZ group was increased from 330 mg/dL at 0 week to 530 mg/dL at 8 weeks; and after administration of Januvia for 8 weeks, the value of blood glucose in the mice of the DPP4I group was effectively maintained at 330 mg/dL. After administration of PPD for 8 weeks, blood glucose in the mice was increased slightly from 330 mg/dL at 0 week to 400 mg/dL. In the negative control group, blood glucose in the mice was stably maintained at 180 mg/dL. From the test results, it is clearly observed that when the dose of PPD used is 1.8% of the Januvia dose, blood glucose is highly effectively modulated.

Effects of PPF on Blood Glucose in the Diabetic Mice

Figure 15:
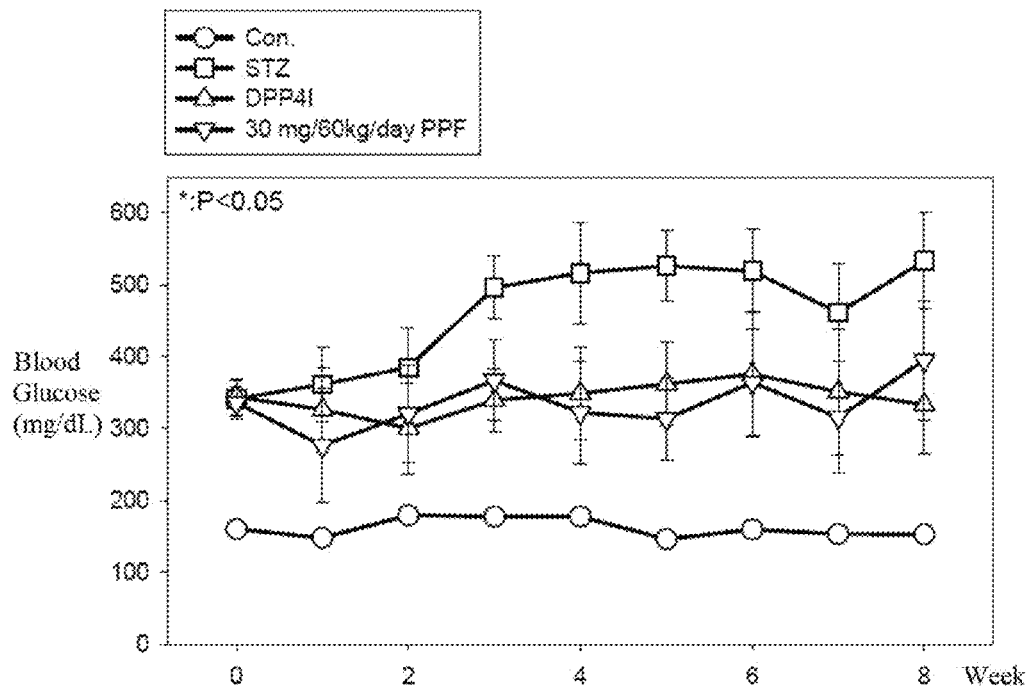
FIG. 15 shows the variation of blood glucose in the mice after administration of PPF.

The dose of PPF administered was 4.5 mg/kg/mouse, equivalent to the dose of 30 mg/day for an adult human of 60 kg. PPF was administered by gavage to the mice at the fixed time of every day, for total of 8 weeks. FIG. 15 shows variation of blood glucose in the mice after administration of PPF. As shown in FIG. 15, the value of blood glucose in the mice of the STZ group was increased from 330 mg/dL at 0 week to 530 mg/dL at 8 weeks; and after administration of Januvia for 8 weeks, the value of blood glucose in the mice of the DPP4I group was effectively maintained at 330 mg/dL. After administration of PPF for 8 weeks, blood glucose in the mice was slightly increased from 330 mg/dL at 0 week to 398 mg/dL. In the negative control group, blood glucose in the mice was stably maintained at 180 mg/dL. From the test results, it is clearly observed that when the dose of PPF used is 1.2% of the Januvia dose, blood glucose is effectively highly modulated.

Effects of PPG on Blood Glucose in the Diabetic Mice

Figure 16:
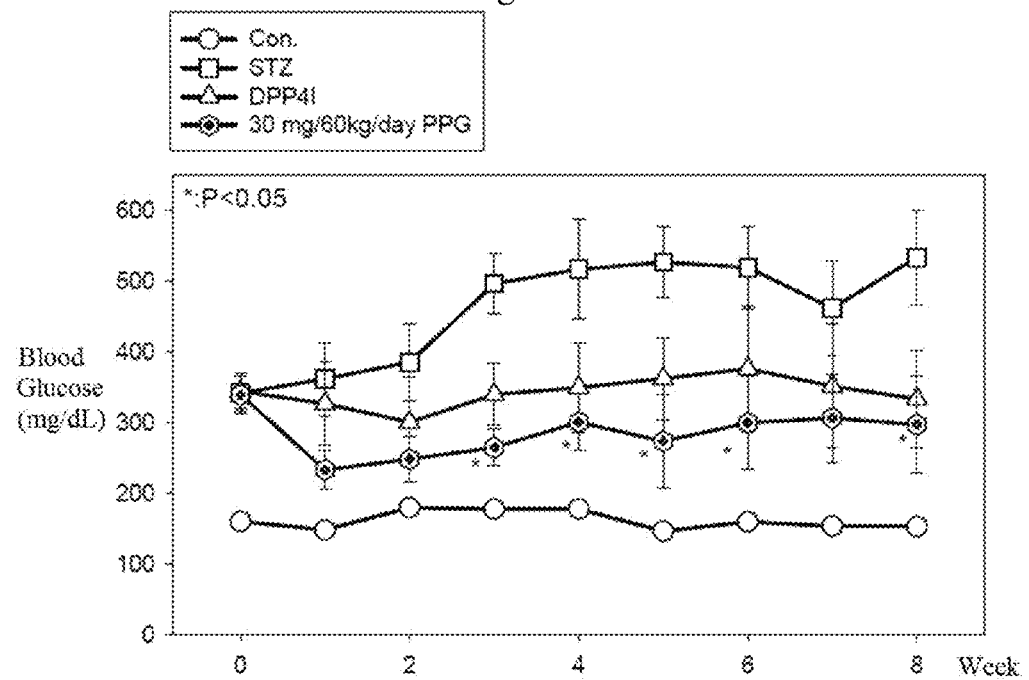
FIG. 16 shows the variation of blood glucose in the mice after administration of PPG.

The dose of PPG administered was 4.5 mg/kg/mouse, equivalent to the dose of 30 mg/day for an adult human of 60 kg. PPG was administered by gavage to the mice at the fixed time of every day, for total of 8 weeks. FIG. 16 shows variation of blood glucose in the mice after administration of PPG. As shown in FIG. 16, the value of blood glucose in the mice of the STZ group was increased from 330 mg/dL at 0 week to 530 mg/dL at 8 week; and after administration of Januvia for 8 weeks, the value of blood glucose in the mice of the DPP4I group was effectively maintained at 330 mg/dL. After administration of PPG for 8 weeks, blood glucose in the mice was slightly reduced from 330 mg/dL at 0 week to 298 mg/dL. Surprisingly, the values of blood glucose of the PPG group are all lower than those of the DPP4I group, let alone that the dose of PPG used is 1.2% of the Januvia dose. Thus, PPG has a higher activity for modulation of blood glucose than DPP4I. In the negative control group, blood glucose in the mice was stably maintained at 180 mg/dL. From the test results, it is clearly observed that PPG is the most effective compound for modulating blood glucose.

Effects of PPC, PPD, PPF and PPG on Feedstuff Intake of the Diabetic Mice

FIGS. 17 to 20 show a variation of food intake of the mice after administration of PPC, PPD, PPF and PPG, respectively. In the mice of the STZ group, the feedstuff intake was 8.0 g/mouse at 1 week, was increased to 15.0 g/mouse at 6 weeks, and was 12.5 g/mouse at 8 weeks. In the mice of the DPP4I group, the feedstuff intake was 5.5 g/mouse at 1 week, was increased to 6.5 g/mouse at 6 weeks, and still remained at 6.4 g/mouse at 8 weeks. In the mice of the negative control group, the feedstuff intake was 5.1 g/mouse at 1 week, was increased to 5.4 g/mouse at 6 weeks, and reduced to 5.1 g/mouse at 8 weeks.

Figure 17:
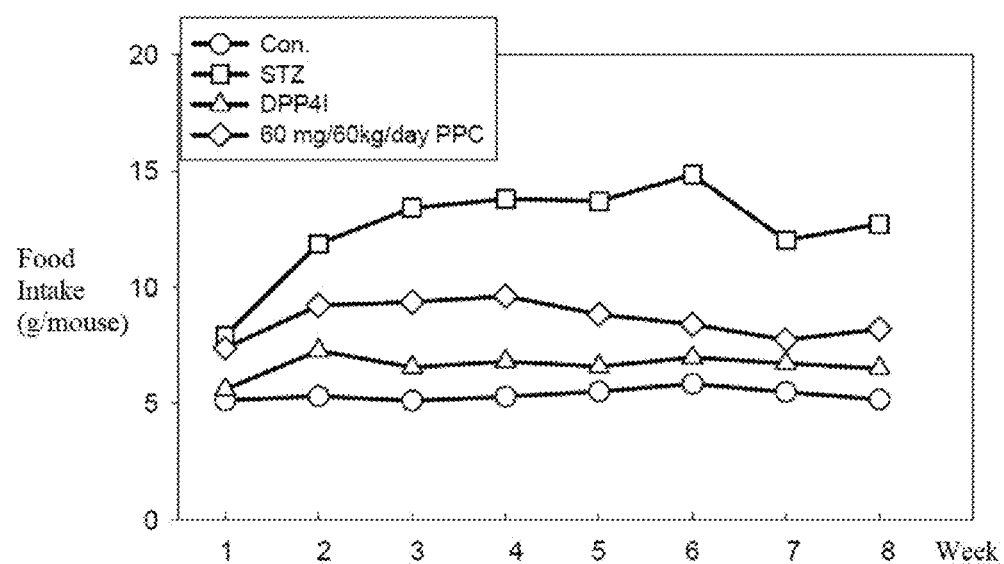
FIG. 17 shows the variation of food intake of the mice after administration of PPC.
Figure 18:
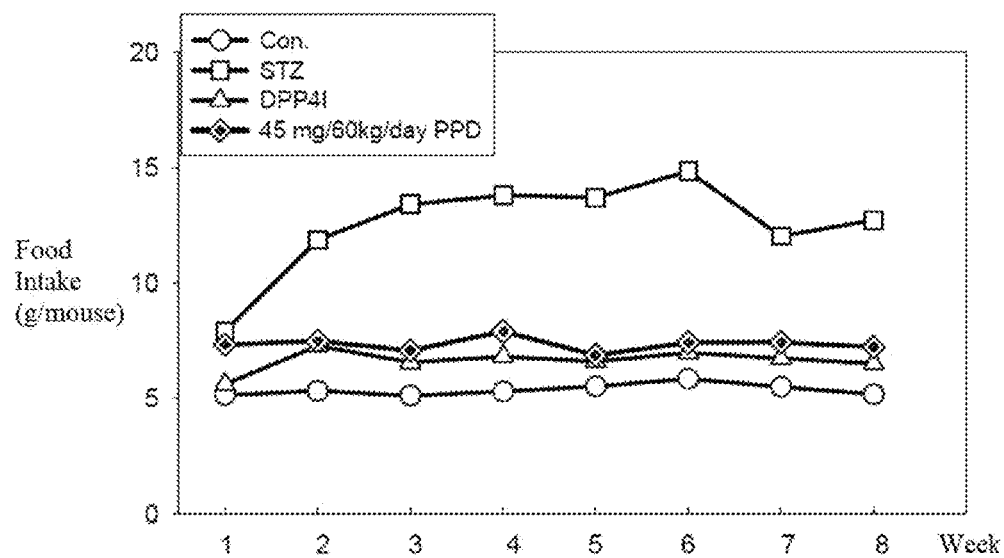
FIG. 18 shows the variation of food intake of the mice after administration of PPD.
Figure 19:
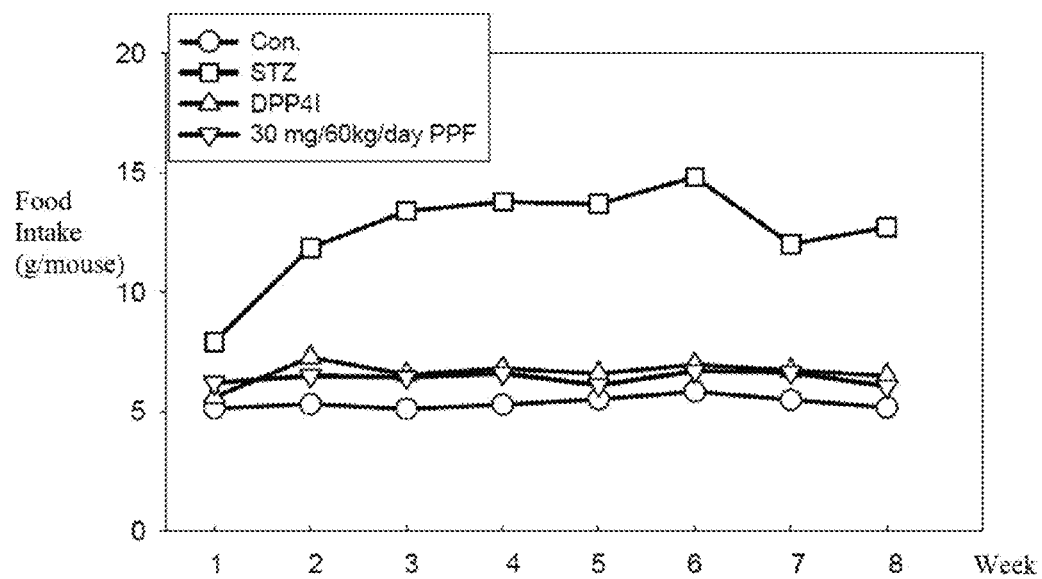
FIG. 19 shows the variation of food intake of the mice after administration of PPF.
Figure 20:
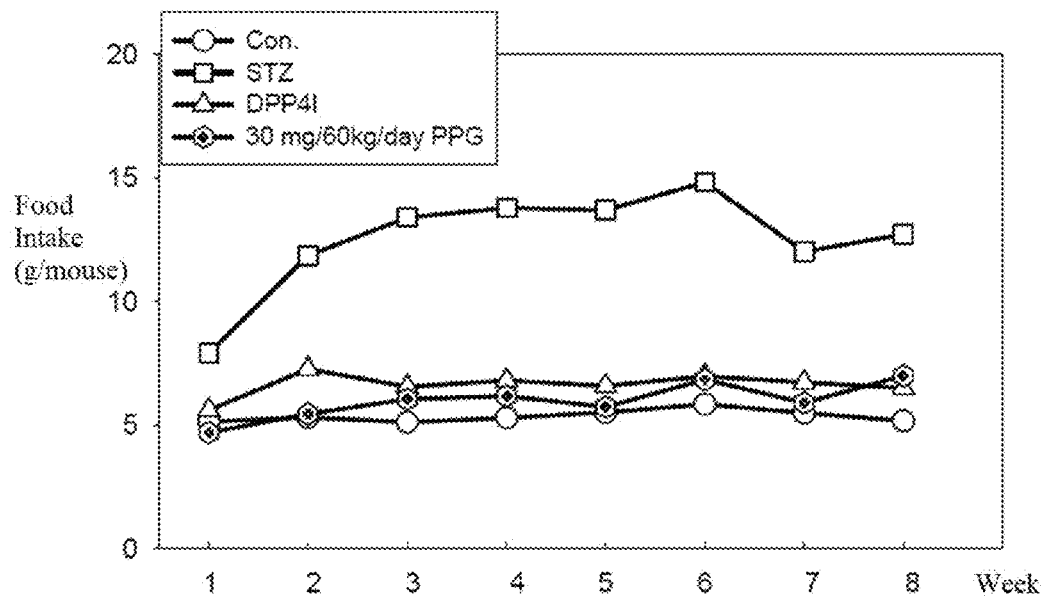
FIG. 20 shows the variation of food intake of the mice after administration of PPG.

As shown in FIG. 17, in the mice of the PPC group, the feedstuff intake was 7.2 g/mouse at 1 week, was increased to 8.0 g/mouse at 6 weeks, and still remained 7.9 g/mouse at 8 weeks. In the mice of the PPD group, the feedstuff intake was 7.2 g/mouse at 1 week and still remained 7.2 g/mouse at 6 weeks and at 8 weeks. As shown in FIG. 19, in the mice of the PPF group, the feedstuff intake was 6.3 g/mouse at 1 week, was increased to 7.0 g/mouse at 6 weeks, and was decreased to 6.3 g/mouse at 8 weeks. As shown in FIG. 20, in the mice of the PPG group, the feedstuff intake was 4.8 g/mouse at 1 week, was increased to 7.0 g/mouse at 6 weeks, and still remained 7.2 g/mouse at 8 weeks.

From the test results, it is clearly observed that PPC, PPD, PPF and PPG significantly inhibited feedstuff intake of the diabetic mice, so the propolins indeed enable improvement of blood glucose in the mice, and without excess feedstuff intake for the mice.

Effects of PPC, PPD, PPF and PPG on Water Intake of the Diabetic Mice

FIGS. 17 to 20 show a variation of water intake of the mice after administration of PPC, PPD, PPF and PPG, respectively. In the mice of the negative control group, the water intake was 4.0 mL/mouse at 1 week, was increased to 3.5 mL/mouse at 6 weeks, and still remained at 3.5 mL/mouse at 8 weeks. In the mice of the STZ group, the water intake was 10.5 mL/mouse at 1 week, was increased to 27.0 mL/mouse at 6 weeks, and was 23.5 mL/mouse at 8 weeks. In the mice of the DPP4I group, the water intake was 8.0 mL/mouse at 1 week, was increased to 12.0 mL/mouse at 6 weeks, and still remained at 12.5 mL/mouse at 8 weeks.

Figure 21:
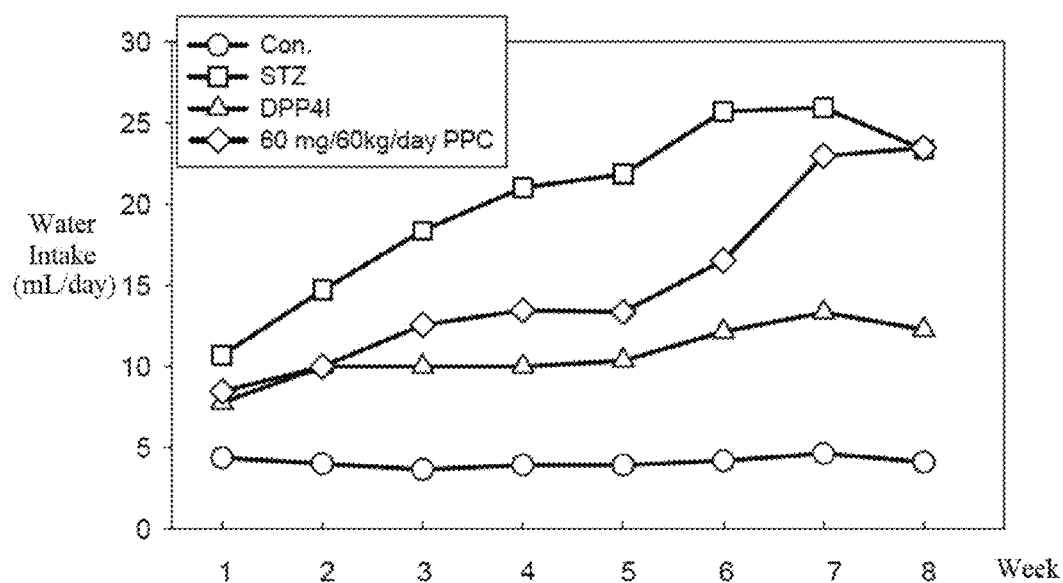
FIG. 21 shows the variation of water intake of the mice after administration of PPC.
Figure 22:
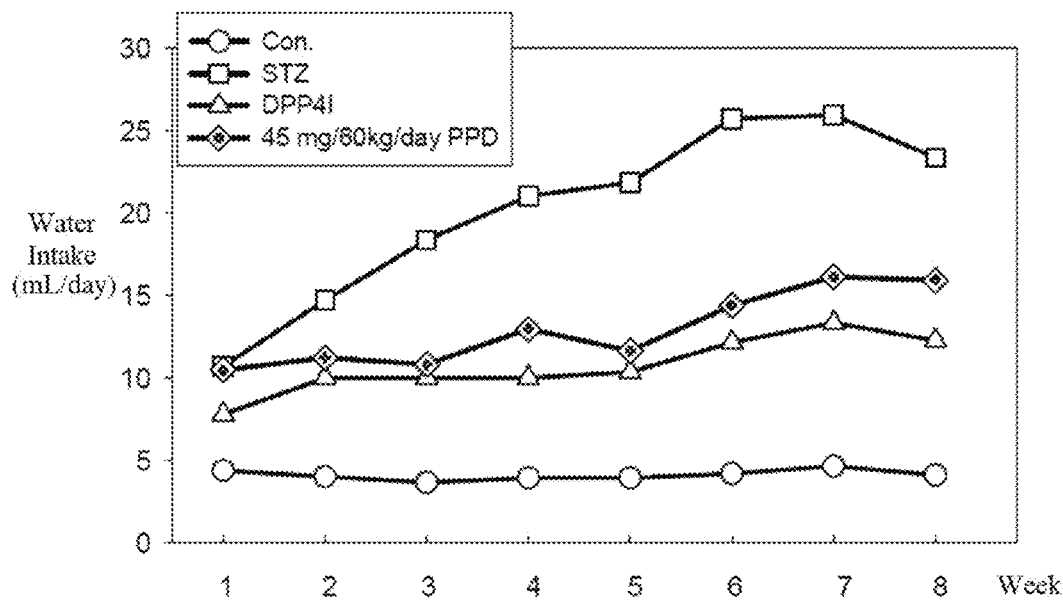
FIG. 22 shows the variation of water intake of the mice after administration of PPD.
Figure 23:
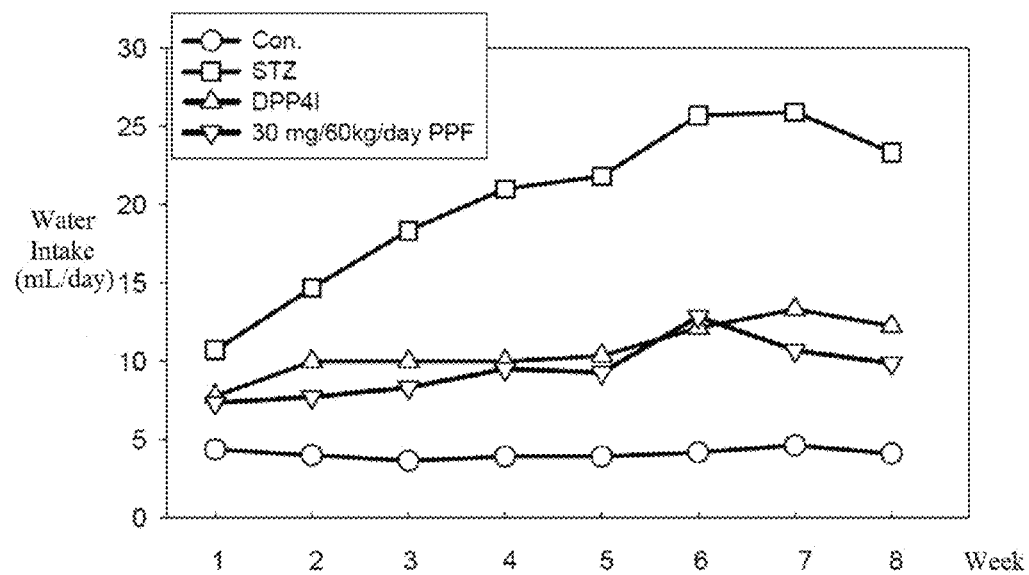
FIG. 23 shows the variation of water intake of the mice after administration of PPF.
Figure 24:
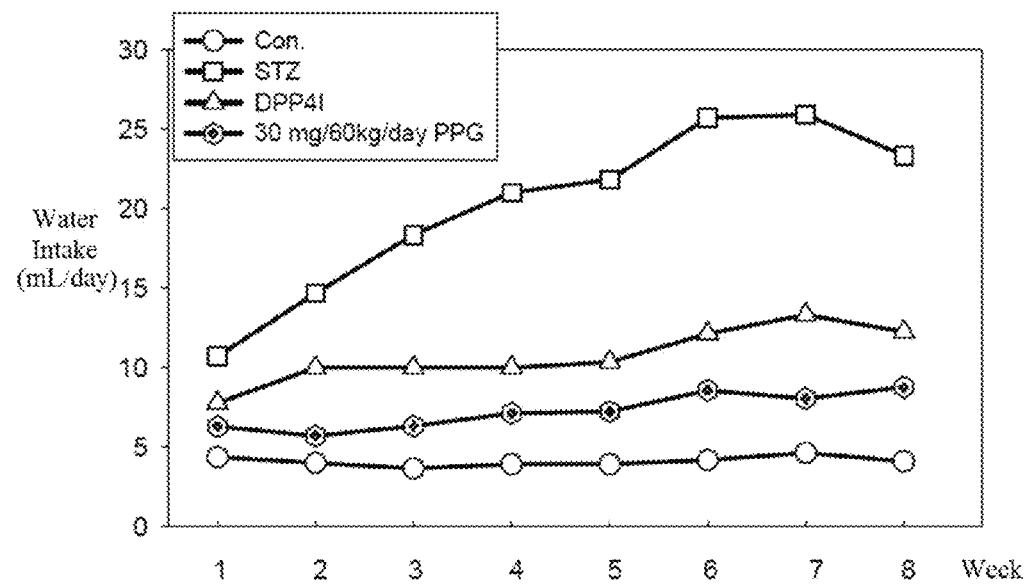
FIG. 24 shows the variation of water intake of the mice after administration of PPG.

As shown in FIG. 21, in the mice of the PPC group, the water intake was 8.2 mL/mouse at 1 week, was increased to 16.0 mL/mouse at 6 weeks, and was 24.0 mL/mouse at 8 weeks. As shown in FIG. 22, in the mice of the PPD group, the water intake was 8.0 mL/mouse at 1 week, was increased to 14.0 mL/mouse at 6 weeks, and was 16.0 mL/mouse at 8 weeks. As shown in FIG. 23, in the mice of the PPF group, the water intake was 8.0 mL/mouse at 1 week, was increased to 13.0 mL/mouse at 6 weeks, and was decreased to 10.0 mL/mouse at 8 weeks. As shown in FIG. 24, in the mice of the PPG group, the water intake was 6.5 mL/mouse at 1 week, was increased to 9.0 mL/mouse at 6 weeks, and still remained 9.0 mL/mouse at 8 weeks.

From the test results, it is clearly observed that the propolins can reduce blood glucose, such that the mice need not excess water intake. In the embodiments of the application, PPC and PPD can significantly inhibited water intake of the diabetic mice, and have higher efficacy then the commercial drug DPP4I.

Efficacy of PPC, PPD, PPF and PPG in the Glucose Tolerance Test

FIGS. 25 to 28 show a variation of blood glucose of the mice after administration of PPC, PPD, PPF and PPG in the glucose tolerance test. In the mice of the negative control group, the value of blood glucose was about 190 mg/dL at 0 point, peaked to about 240 mg/dL at the 30-minute time point after administration of glucose in water, was 190 mg/dL at the 120-minute time point, and was reduced to 140 mg/dL at the 180-minute time point. In the mice of the STZ group, the value of blood glucose was about 470 mg/dL at 0 point, peaked to about 590 mg/dL at the 30-minute time point after administration of glucose in water, was about 520 mg/dL at the 120-minute time point, and still remained at 520 mg/dL at the 180-minute time point. In the mice of the DPP4I group, the value of blood glucose was about 380 mg/dL at 0 point, peaked to about 450 mg/dL at the 30-minute time point after administration of glucose in water, was about 450 mg/dL at the 120-minute time point, and was 400 mg/dL at the 180-minute time point.

Figure 25:
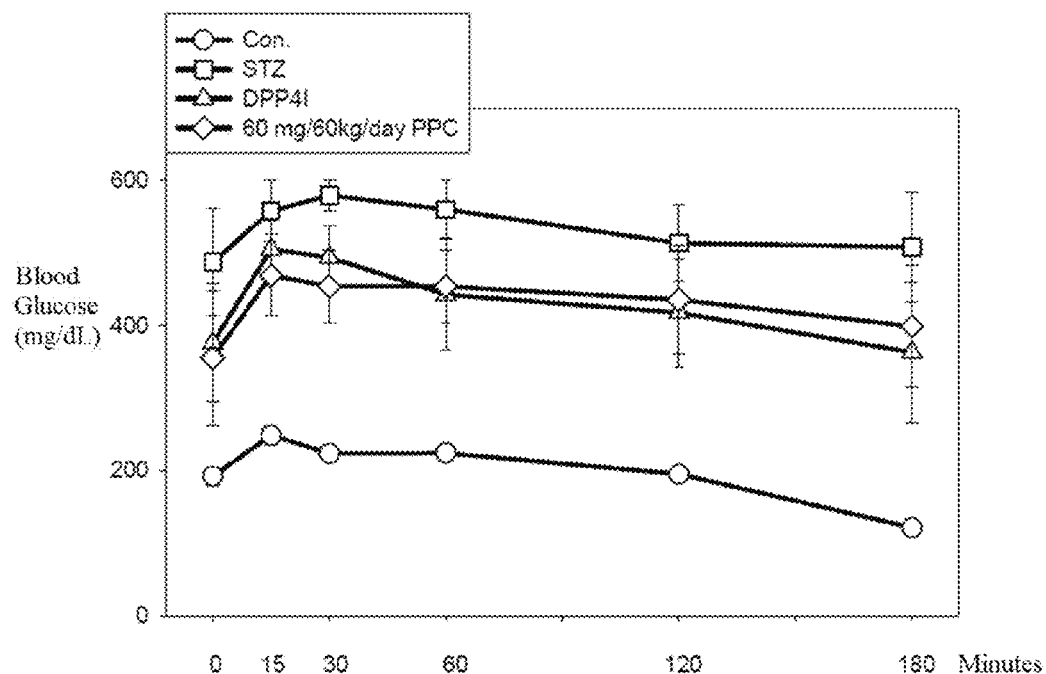
FIG. 25 shows the variation of blood glucose of the mice after administration of PPC.

As shown in FIG. 25, in the mice of the PPC group, the value of blood glucose was about 350 mg/dL at 0 point, peaked to about 450 mg/dL at the 30-minute time point after administration of glucose in water, was about 430 mg/dL at the 120-minute time point, and was reduced to 400 mg/dL at the 180-minute time point.

Figure 26:
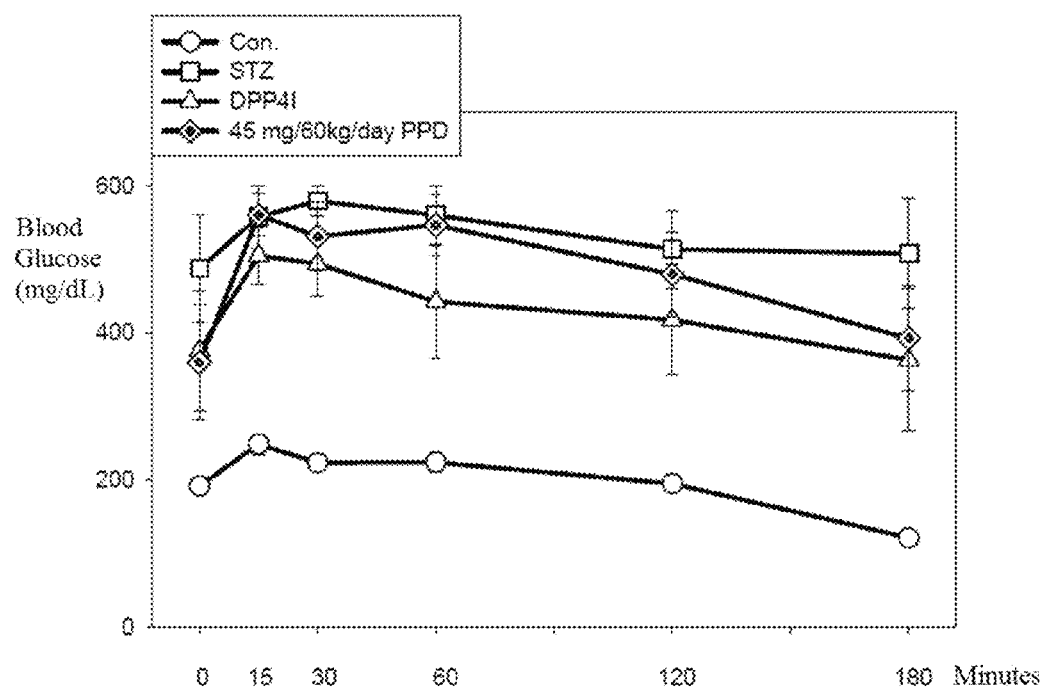
FIG. 26 shows the variation of blood glucose of the mice after administration of PPD.

As shown in FIG. 26, in the mice of the PPD group, the value of blood glucose was about 380 mg/dL at 0 point, peaked to about 530 mg/dL at the 30-minute time point after administration of glucose in water, was about 490 mg/dL at the 120-minute time point, and was reduced to 460 mg/dL at the 180-minute time point.

Figure 27:
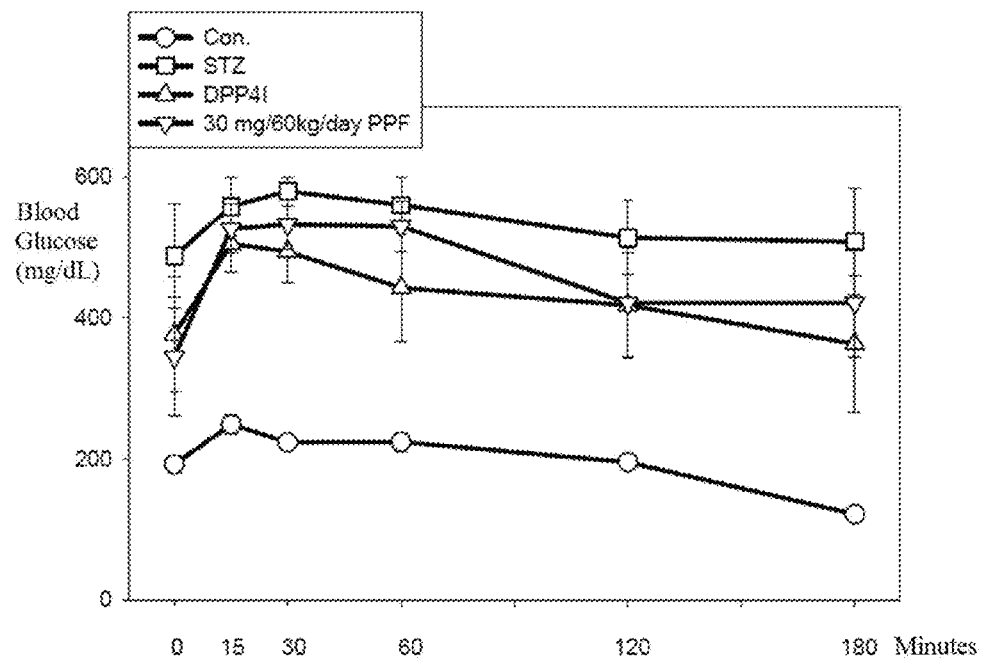
FIG. 27 shows the variation of blood glucose of the mice after administration of PPF.

As shown in FIG. 27, in the mice of the PPF group, the value of blood glucose was about 390 mg/dL at 0 point, peaked to about 525 mg/dL at the 30-minute time point after administration of glucose in water, was about 420 mg/dL at the 120-minute time point, and remained 430 mg/dL at the 180-minute time point.

Figure 28:
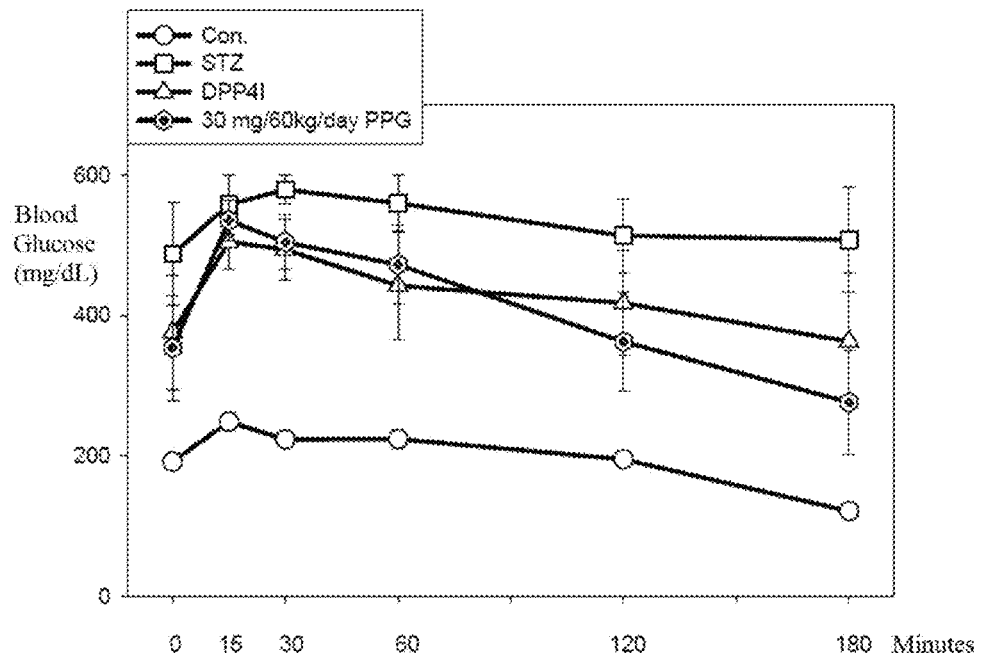
FIG. 28 shows the variation of blood glucose of the mice after administration of PPG.

As shown in FIG. 28, in the mice of the PPG group, the value of blood glucose was about 385 mg/dL at 0 point, peaked to about 525 mg/dL at the 30-minute time point after administration of glucose in water, was about 380 mg/dL at the 120-minute time point, and was reduced to 350 mg/dL at the 180-minute time point.

From the test results, it is clearly observed that in the normal mice, the beta cells are able to normally secrete insulin, and the value of blood glucose is less high at the 30-minute time point after administration of glucose in water due to rapid absorption and utilization of glucose in the cells, and returns back to the 0 point value of blood glucose at the 120-minute time point. In the mice of the PPG group, the value of blood glucose was very high at the 30-minute time point after administration of glucose in water due to very slow absorption and utilization of glucose in the cells, but glucose was rapidly absorbed and utilized over the period of 30 to 120 minutes, and returned to the 0 point blood glucose value at the 120-minute time point. From this test result, it is concluded that the propolins is involved in a mechanism of enhancing subsequent absorption of glucose in the cells instead of promotion of insulin secretion.

FIGS. 29 to 32 show an AUC graph of blood glucose in the mice after administration of PPC, PPD, PPF and PPG, respectively, calculated in integral area with time at the X-axis versus the blood glucose value at the Y-axis, and analyzed by the sigma plot software.

Figure 29:
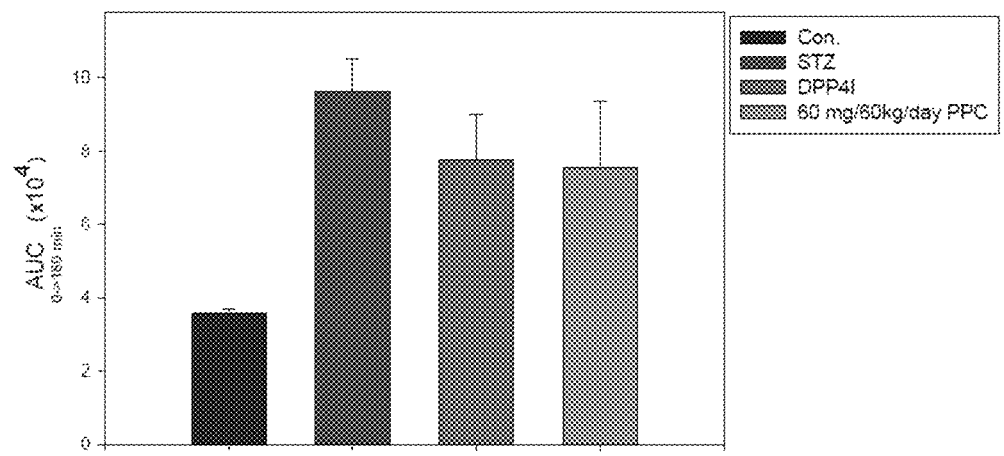
FIG. 29 shows an AUC graph of blood glucose in the mice after administration of PPC.
Figure 30:
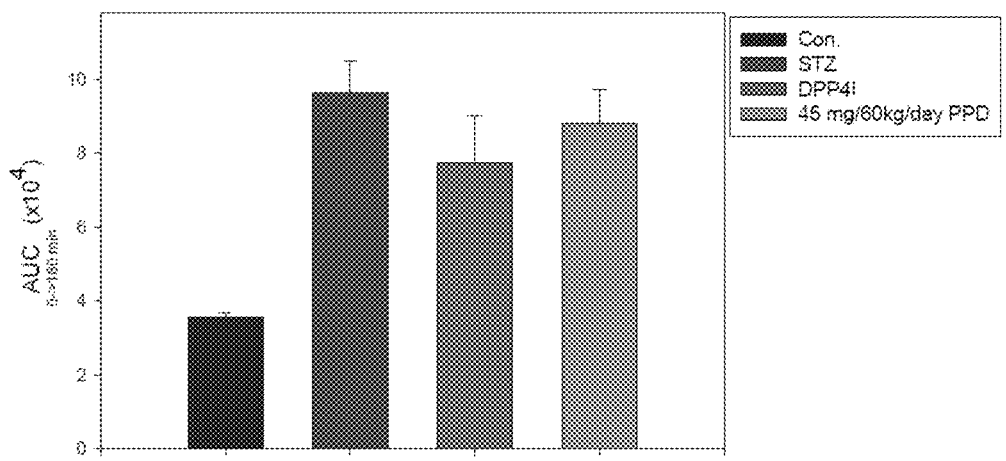
FIG. 30 shows an AUC graph of blood glucose in the mice after administration of PPD.
Figure 31:
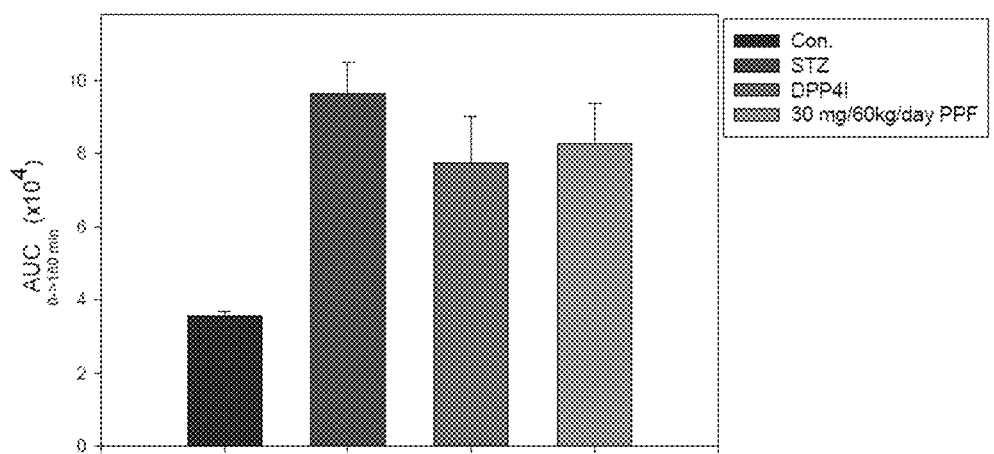
FIG. 31 shows an AUC graph of blood glucose in the mice after administration of PPF.
Figure 32:
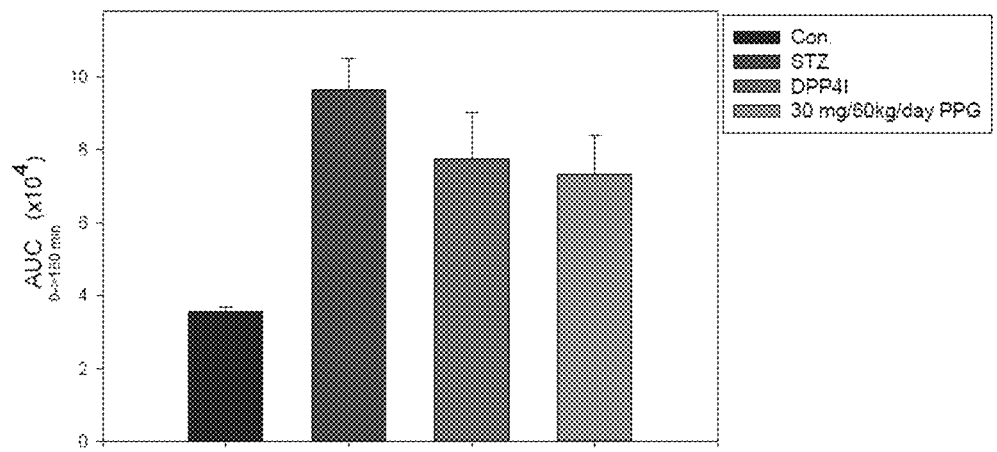
FIG. 32 shows an AUC graph of blood glucose in the mice after administration of PPG.

In the mice of the negative control group, due to normal functions as insulin secretion from the beta cells, it has a minimal integral area with an AUC value of about $3.8 \times 10^4$. In the mice of the STZ group, since the beta cells are damaged and the insulin secretion is low, it has a maximal integral area with an AUC value of about $9.65 \times 10^4$. In the mice of the DPP4I group, due to a part of the functions of the beta cells are restored and the basic insulin secretion is maintained, it has a significantly reduced integral area with an AUC value of about $7.2 \times 10^4$, when compared to the STZ group. As shown in FIG. 29, the AUC value for blood glucose in the mice of the PPC group was about $8.0 \times 10^4$. As shown in FIG. 30, the AUC value for blood glucose in the mice of the PPD group was about $8.7 \times 10^4$. As shown in FIG. 31, the AUC value for the mice of the PPF group was about $8.2 \times 10^4$. As shown in FIG. 32, the AUC value for blood glucose in the mice of the PPG group was about $7.8 \times 10^4$. From this test result, it is clearly observed that the propolins indeed enable restoration of a part of the functions of the beta cells and maintenance of basic insulin secretion.

When compared to the DPP4I (Januvia) group and the PPC, PPD, PPF and PPG groups, respectively, the extent of reduction for the STZ group was 42.0%, 28.2%, 16.2%, 15.0%, 31.7%, respectively, wherein the dose of PPC used was 2.4% of the Januvia dose only, the dose of PPD used was 1.8% of the Januvia dose only, the dose of PPF uses was 1.2% of the Januvia dose only, and the dose of PPG used was 1.2% of the Januvia dose only. From this test result, it is clearly observed that the low dose of propolins is effective for modulation of blood glucose, and especially PPG has more excellent efficacy.

From the test results above, the propolins indeed enable effective modulation of blood glucose, reduction of feedstuff intake of the mice, and significant reduction of water intake. It is indicated in the glucose tolerance test (OGTT) that in the mice of the propolins-fed group, blood glucose is significantly restored and reduced when compared to the STZ group. On the other hand, it is indicated from the test results of glycosylated hemoglobin (HbA1c) as biochemical indicator that, in the mice of the propolins-fed group, HbA1c is significantly reduced when compared to the STZ group. Therefore, the compounds of formula (1) provided by the present invention, including propolins in various Taiwan Green Propolis and analogs thereof, indeed have the activity for modulation of blood glucose and may be used for preparation of the drugs for diabetes.

We claim:
1. A method for modulating blood glucose in a subject in need thereof, comprising administering to the subject an effective amount of a compound selected from the following:

(S,E)-2-(3,4-dihydroxyphenyl)-6-(3,7-dimethylocta-2,6-dien-1-yl)-5,7-dihydroxy-3,4-dihydro-2H-1-benzopyran-4-one (PPC)

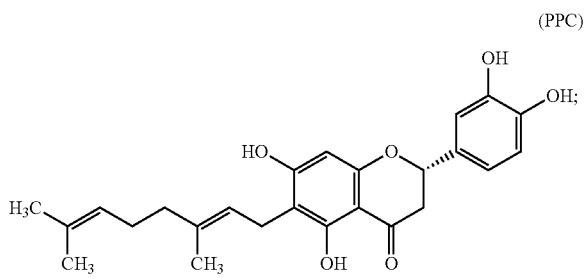 [SMILES: CC(C)=CCC/C(C)=C/Cc1c(O)cc2c(c1O)C(=O)C[C@@H](c1ccc(O)c(O)c1)O2]

(S,E)-2-(2-(3,7-dimethylocta-2,6-dien-1-yl)-3,4-dihydroxyphenyl)-5,7-dihydroxy-3,4-dihydro-2H-1-benzopyran-4-one (PPD)

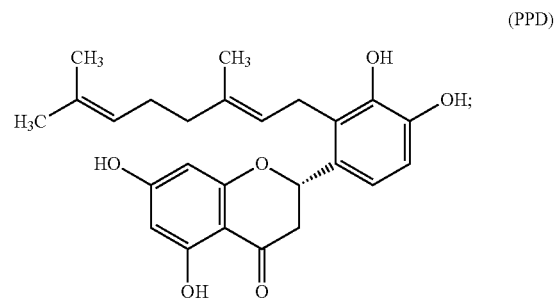 [SMILES: CC(C)=CCC/C(C)=C/Cc1c([C@@H]2CC(=O)c3c(O)cc(O)cc3O2)ccc(O)c1O]

(S,E)-2-(3-(3,7-dimethylocta-2,6-dien-1-yl)-4,5-dihydroxyphenyl)-5,7-dihydroxy-3,4-dihydro-2H-1-benzopyran-4-one (PPF)

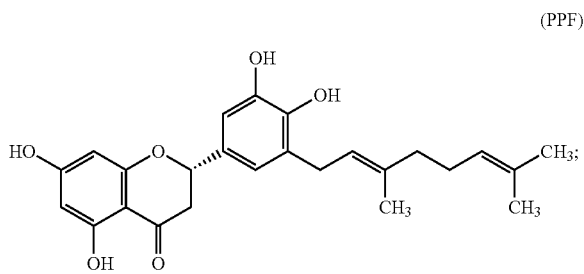 [SMILES: CC(C)=CCC/C(C)=C/Cc1cc([C@@H]2CC(=O)c3c(O)cc(O)cc3O2)cc(O)c1O]

(S,E)-2-(2-(3,7-dimethylocta-2,6-dien-1-yl)-3,4-dihydroxyphenyl)-5,5,7-dihydroxy-6-(3-methylbut-2-en-1-yl)-3,4-dihydro-2H-1-benzopyran-4-one (PPG)

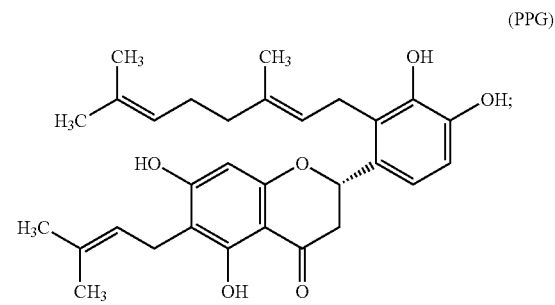 [SMILES: CC(C)=CCC/C(C)=C/Cc1c([C@@H]2CC(=O)c3c(cc(O)c(CC=C(C)C)c3O)O2)ccc(O)c1O]

(S)-2-(3,4-dihydroxyphenyl)-5,7-dihydroxy-6-((2E,6E)-3,7,11-trimethyldodeca-2,6,10-trien-1-yl)-3,4-dihydro-2H-1-benzopyran-4-one (PPI)

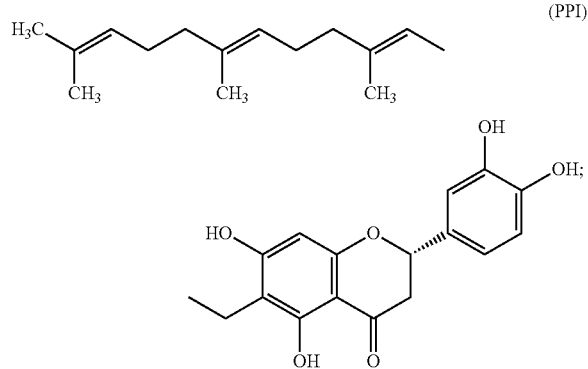

(S,E)-2-(3,4-dihydroxy-2-(7-hydroxy-3,7-dimethyloct-2-en-1-yl)phenyl)-5,7-dihydroxy-3,4-dihydro-2H-1-benzopyran-4-one (PPA)

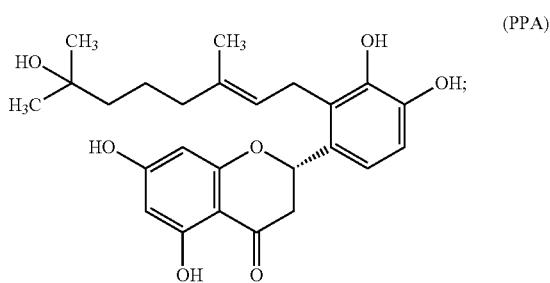 [SMILES: C/C(=C\Cc1c([C@@H]2CC(=O)c3c(O)cc(O)cc3O2)ccc(O)c1O)CCCC(C)(C)O]

10  (S,E)-2-(3,4-dihydroxy-5-(7-hydroxy-3,7-dimethyloct-2-en-1-yl)phenyl)-5,7-dihydroxy-3,4-dihydro-2H-1-benzopyran-4-one (PPB)

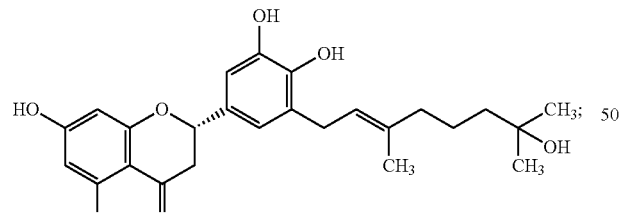

(S,E)-2-(3,4-dihydroxyphenyl)-5,7-dihydroxy-6-(7-hydroxy-3,7-dimethyloct-2-en-1-yl)-3,4-dihydro-2H-1-benzopyran-4-one (Pokinawan)

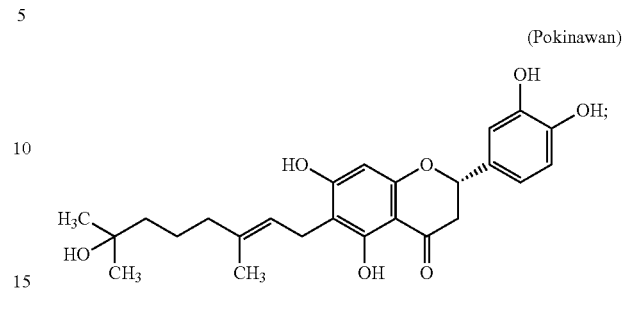

(S,E)-2-(3,4-dihydroxy-2-(7-hydroxy-3,7-dimethyloct-2-en-1-yl)phenyl)-5 5,7-dihydroxy-6-(3-hydroxy-3-methylbutyl)-3,4-dihydro-2H-1-benzopyran-4-one

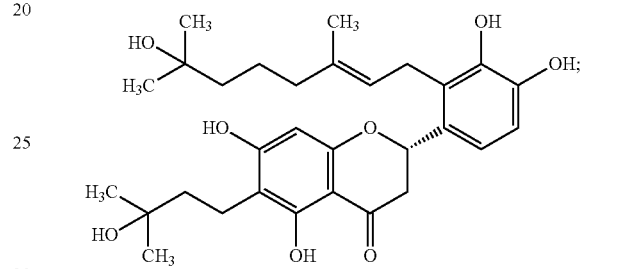

and
(S)-2-(3,4-dihydroxyphenyl)-5,7-dihydroxy-6-((2E,6E)-11-hydroxy-3,7,11-trimethyldodeca-2,6-dien-1-yl)-3,4-dihydro-2H-1-benzopyran-4-one

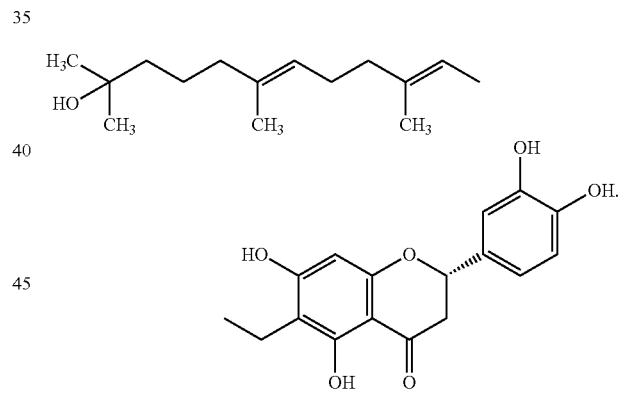

2. The method of claim 1, wherein the compound can be used for treating or preventing diabetes.

3. The method of claim 2, wherein the diabetes is type II diabetes.

4. The method of claim 1, wherein the compound is used as drugs, healthy food or food supplements.

* * * * *